United States Patent [19]
Sawada et al.

[11] Patent Number: 5,094,533
[45] Date of Patent: Mar. 10, 1992

[54] OPTOELECTRICAL PARTICLE DETECTION APPARATUS

[75] Inventors: Shigetomo Sawada, Isehara; Kazuo Kobayashi, Ayase, both of Japan

[73] Assignee: Fujitsu Limited, Kawasaki, Japan

[21] Appl. No.: 657,989

[22] Filed: Feb. 21, 1991

Related U.S. Application Data

[63] Continuation of Ser. No. 286,624, Dec. 19, 1988, abandoned.

[30] Foreign Application Priority Data

Dec. 18, 1987 [JP] Japan ............................ 62-321829

[51] Int. Cl.⁵ .................... G01N 21/47; G01N 15/02
[52] U.S. Cl. .................................. 356/338; 359/860; 359/863
[58] Field of Search ............ 356/336, 337, 338, 339; 350/620, 622, 623, 624

[56] References Cited

U.S. PATENT DOCUMENTS

| | | | |
|---|---|---|---|
| 3,414,354 | 12/1968 | Siegler | 350/622 |
| 3,578,867 | 5/1971 | Barrington | 356/338 |
| 4,739,177 | 4/1988 | Borden | 356/338 |
| 4,825,094 | 4/1989 | Borden et al. | 356/338 |
| 4,848,905 | 7/1989 | Iino | 356/338 |

FOREIGN PATENT DOCUMENTS 0231542 12/1986 European Pat. Off. .
1547360 7/1966 Fed. Rep. of Germany .
1168717 10/1969 United Kingdom ............... 350/620

OTHER PUBLICATIONS

Patent Abstracts of Japan, vol. 12, No. 23 (P-658) (2370), 1/23/88; & JP A-62177432 (Kowa Co) 8/4/87.
Patent Abstracts of Japan, vol. 6, No. 112 (P-124) (990), 6/23/82; & JP A-57042842 (Nitsutan K.K.) 3/10/82.
Patent Abstracts of Japan, vol. 11, No. 93, (P-559) (2540), 3/24/87; & JP A-61245041 (Fujitsu Ltd.) 10/31/86.

*Primary Examiner*—Richard A. Rosenberger
*Attorney, Agent, or Firm*—Staas & Halsey

[57] ABSTRACT

An optoelectrical particle detection apparatus comprising concave and convex reflectors spaced from each other by a predetermined distance, a laser source for emitting a laser beam and introducing the laser beam between the concave and convex reflectors, the concave and convex reflectors and the laser source being arranged so that the laser beam is multi-reflected at a much closer pitch to form a laser beam curtain in which the multi-reflected beam segments are overlapped with respect to each other to enhance a light intensity thereof, and an optoelectrical detector for receiving light scattered due to a presence of particles in the laser beam curtain, whereby the presence of particles can be detected in the laser beam curtain with a high probability and a high sensitivity.

17 Claims, 28 Drawing Sheets

MIRROR
SHIFT 0 mm 50 mm

NUMBER OF REFLECTIONS >100

MIRROR
SHIFT 0.2mm

NUMBER OF REFLECTIONS 47

MIRROR
SHIFT 0.4mm

NUMBER OF REFLECTIONS 35

MIRROR
SHIFT 0.6mm

NUMBER OF REFLECTIONS 29

MIRROR
SHIFT 0.8mm

NUMBER OF REFLECTIONS 25

MIRROR
SHIFT 1.0mm

NUMBER OF REFLECTIONS 23

Fig. 18A
Fig. 18B
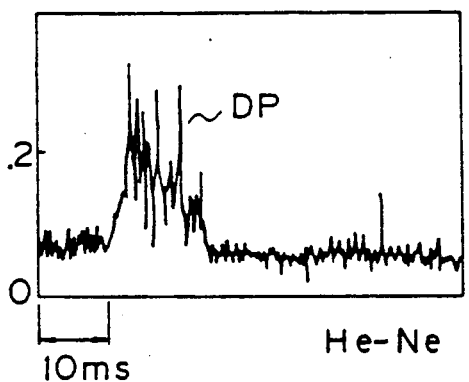
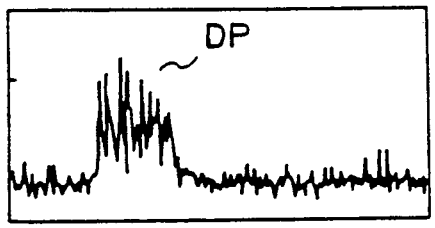
He-Ne LASER (2mW)
Fig. 19A
Fig. 19B
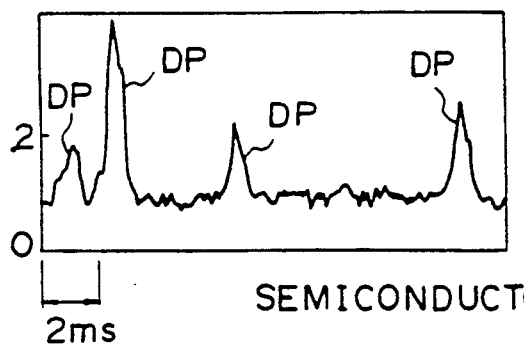
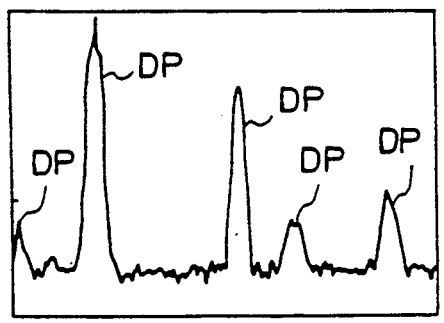
SEMICONDUCTOR LASER (8mW)
Fig. 20A
Fig. 20B
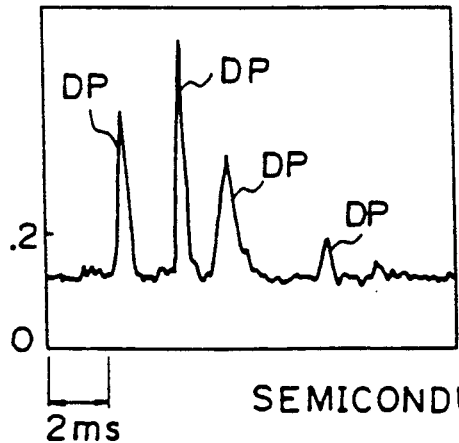
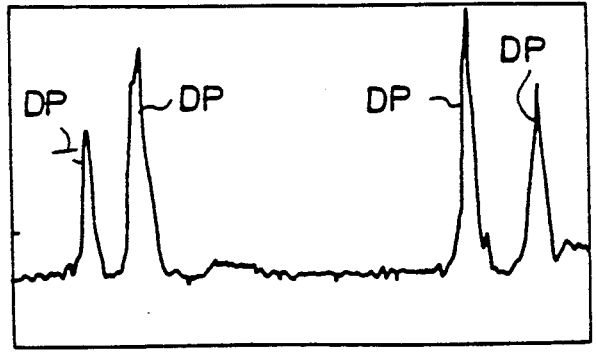
SEMICONDUCTOR LASER (3.9mW)

SEMICONDUCTOR LASER(5.5mW)

SEMICONDUCTOR LASER (37mW)
SHEET BEAM

OPTOELECTRICAL PARTICLE DETECTION APPARATUS

This application is a continuation of application Ser. No. 286,624, filed Dec. 19, 1988, now abandoned.

BACKGROUND OF THE INVENTION (1) Field of the Invention

The present invention relates to an apparatus for optoelectrically detecting floating particles in ambience by using a laser beam, and in particular, relates to such an optoelectrical particle detection apparatus which can be advantageously used to detect floating particles in a closed ambience such as a clean room for the production of semi-conductors, and a vacuum chamber for the formation of a thin film by, for example, a vacuum evaporation process, a sputtering process and a chemical vapor deposition process.

(2) Description of the Related Arts

An optoelectrical particle detection apparatus is well known, as disclosed in, for example, U.S. Pat. No. 4,655,592 and U.S. Pat. No. 4,422,761. U.S. Pat. No. 4,655,592 is directed to an apparatus for optoelectrically detecting particles on a surface of a substrate, wherein a light emitted from a light source is focused on the substrate surface as a small spot through an optical system, and wherein a light detector such as a photomultiplier tube for receiving a light scattered from the small light spot due to a presence of a particle therewithin is provided. U.S. Pat. No. 4,422,761 is directed to an apparatus for optoelectrically detecting floating particles in air, wherein a light emitted from a light source is focused on an inspection point through an optical system, an air flow including particles to be detected being continuously passed through the inspection point, and wherein a light detector such as a photomultiplier tube for receiving a light deflected or scattered from the inspection point due to the presence of particles included in the air flow is provided.

As apparent from the foregoing, in an optoelectrical particle detection apparatus of the types disclosed in U.S. Pat. Nos. 4,655,592 and 4,422,761, the zone in which the presence of particles can be detected is very restricted, and thus it is impossible or very difficult to effectively detect the presence of particles over a large area. In addition, the apparatus of U.S. Pat. No. 4,655,592 can not be adapted for the detection of particles in a vacuum chamber for the formation of a thin film element, as mentioned above, because it is impossible to use a medium such as an air flow entraining the particles passing the inspection point.

Unexamined Japanese Patent Publication No. 61-240645 discloses an optoelectrical particle detection apparatus wherein a scanning laser beam is used to widen a zone in which the presence of particles can be detected, and wherein a TV camera is provided for receiving light scattered from the scanning beam due to the presence of particles in the scanning zone. In a detection apparatus of this type, however, since particles to be detected have a higher velocity, the particle detection probability becomes lower, and may be equivalent to that of detecting particles by using a non-scanning or single static laser beam. Namely, when particles to be detected have a very high velocity, it is meaningless to widen the detection zone by using a scanning beam.

Also well known is an optoelectrical particle detection apparatus wherein a strong laser beam is used to detect particles, with a high sensitivity. In this apparatus, which is commercially available, a strong laser beam between resonance mirrors of a laser generator is used for particle detection. In a detection of this type, however, the zone for detection of particles is also very restricted due to use of the single laser beam, and the application of this type of particle detection is limited because the detection zone must be provided in the laser generator.

Unexamined Japanese Patent Publication No. 61-243345 discloses another particle detection apparatus wherein a strong laser beam is used for the detection. In this apparatus, a laser generator is provided with an outside second resonator in which an output mirror of the laser generator is utilized as one of the resonance mirrors, and thus a strong laser beam obtained in the second resonator is used for the particle detection. Nevertheless, this apparatus suffers from the same defects as the strong laser beam detection apparatus mentioned above.

In another well known optoelectrical particle detection apparatus including a pair of parallel plane reflectors, a semiconductor laser beam is multi-reflected to form a laser beam curtain of the multi-reflected beam segments as a zone in which floating particles can be detected, whereby the floating particles can be detected over a wide area with a high probability by scattered sensing light due to the presence of particles in the laser beam curtain. A detection apparatus of this type is commercially available from High Yield Technology Inc. of the United States of America.

In this detection apparatus, since it is very difficult to multi-reflect the laser beam at a very close pitch, it is substantially impossible to obtain a laser beam curtain having a uniform light intensity. Accordingly, although the presence of particles is detected in the laser beam curtain, the size of the detected particles cannot be determined because the intensity of the scattered light from the same size of particle differs in accordance with the location of the particle in the laser beam curtain, due to the nonuniform light intensity thereof.

In the multi-reflection type apparatus as mentioned above, the parallel plane reflectors must be precisely positioned with respect to each other to obtain an accurate parallel relationship therebetween before the laser beam curtain can be formed between the plane reflectors, but this positioning of the parallel plane reflectors is very complex and difficult because at least one of the plane reflectors must be angularly adjusted around two axes perpendicular to each other.

SUMMARY OF THE INVENTION

Therefore, an object of the present invention is to provide an optoelectrical particle detection apparatus wherein a laser beam is multi-reflected by a combination of concave and convex reflectors to form a laser beam curtain of multi-reflected beam segments as a zone in which floating particles can be detected, wherein the concave and convex reflectors are arranged in such a manner that the laser beam can be multi-reflected at a much closer pitch, to thus obtain a laser beam curtain in which the multi-reflected beam segments are overlapped with respect to each other so that a light intensity thereof is enhanced, whereby the presence of particles can be detected in the laser beam curtain with a high probability and a high sensitivity.

Another object of the present invention is to provide an optoelectrical particle detection apparatus of the type as mentioned above, wherein the concave and convex reflectors are arranged in such a manner that the laser beam can be multi-reflected at a much closer and uniform pitch, to thus obtain a laser beam curtain in which the multi-reflected beam segments are overlapped with respect to each other so that a light intensity thereof is uniformly enhanced, whereby not only can the presence of particles be detected in the laser beam curtain with a high probability and a high sensitivity, but also a size of the detected particle can be determined.

Another object of the present invention is to provide an optoelectrical particle detection apparatus of the type as mentioned above, wherein a relative position between the concave and convex reflectors can be easily adjusted so that the multi-reflection of a laser beam as defined above occurs between the concave and convex reflectors.

In accordance with the present invention, there is provided an optoelectrical particle detection apparatus which comprises: concave and convex reflectors spaced from each other by a predetermined distance; a laser source for emitting a laser beam and introducing the laser beam between the concave and convex reflectors; the concave and convex reflectors and the laser source being arranged so that the laser beam is multi-reflected at a much closer pitch to form a laser beam curtain in which the multi-reflected beam segments are overlapped with respect to each other to enhance a light intensity thereof; and detection means for detecting light scattered due to a presence of particles in the laser beam curtain, whereby the presence of particles can be detected with a high probability and a high sensitivity.

In the optoelectrical particle detection apparatus, the laser beam is preferably introduced between the concave and convex reflectors so as to be substantially in parallel with an optical axis thereof. The laser beam may be multi-reflected between the concave and convex reflectors and then emitted from the space therebetween at a side opposite to the side having the space through which the laser beam is introduced. The laser beam may be also multi-reflected between the concave and convex reflectors at the side of the space therebetween through which the laser beam is introduced, and then emitted from the same side.

In the optoelectrical particle detection apparatus, the laser source preferably comprises a semiconductor laser device in which an interference of the overlapped multi-reflected beam segments is eliminated. A relatively narrow band of the laser beam curtain, a light intensity of which is relatively uniform, is selected as a detection zone, whereby not only can the presence of particles be detected, but also a size of the detected particle can be measured.

In the optoelectrical particle detection apparatus, the concave and convex reflectors preferably have spherical concave and convex reflecting surfaces, respectively. A means is provided for adjusting a relative position between the concave and convex reflectors in two directions perpendicular to each other and to the optical axis thereof, whereby the arrangement of the concave and convex reflectors and the laser source for obtaining the laser beam curtain concerned can be easily carried out without any angular adjustment of the concave and convex reflectors.

In accordance with the present invention, there is also provided an optoelectrical particle detection apparatus which comprises: partial concave and convex reflectors spaced from each other by a predetermined distance, the reflecting surface of the concave reflector having a concave reflecting zone and a plane reflecting zone smoothly continuing therefrom, the reflecting surface of the convex reflector having a convex reflecting zone and a plane reflecting zone smoothly continuing therefrom; a laser source for emitting a laser beam and introducing the laser beam between the concave and convex reflecting zones of the partial concave and convex reflectors to be multi-reflected to form a laser beam curtain therebetween; the concave and convex reflectors and the laser source being arranged so that a pitch of the beam segments multi-reflected between the concave and convex reflecting zones of the partial concave and convex reflectors becomes closer, and so that the much closer pitch of the beam segments multi-reflected between the plane reflecting zones of the partial concave and convex reflectors is uniformly maintained, whereby the multi-reflected beam segments between the plane reflecting zones of the partial concave and convex reflectors can be form a laser beam curtain having a substantially uniform distribution of light intensity; and detection means for detecting light scattered due to a presence of particles in the portion of the laser beam curtain between the plane reflecting zones of the partial concave and convex reflectors, whereby not only can the presence of particles be detected, but also a size of the detected particles can be measured.

In the optoelectrical particle detection apparatus according to the present invention, the detection means preferably includes an optical filter by which noise is eliminated from the light detected by the detection means.

The optoelectrical particle detection apparatus as mentioned above may be advantageously used to detect floating particles in a vacuum chamber for a thin-film forming process. An assembly of the concave and convex reflectors and the laser source is disposed within the vacuum chamber and housed in a housing in such a manner that the laser beam curtain is exposed to the exterior of the housing, and an inert gas is introduced into the housing, whereby pollution of the concave and convex reflectors by particles generated during the thin-film forming process is prevented. In this case, the detection means includes a light detector disposed outside the vacuum chamber, and a bundle of optical fibers having access to the laser beam curtain through a wall defining the vacuum chamber to transmit the scattered light received thereby to the light detector. Also, the bundle of optical fibers is covered by a tube sealingly passed through the wall of the vacuum chamber. The detection means includes an optical filter by which noise is eliminated from the light detected by the detection means. The detection means includes a light detector disposed outside the vacuum chamber, and a bundle of optical fibers having access to the laser beam curtain through a wall defining the vacuum chamber to transmit the scattered light received thereby to the light detector. The bundle of optical fibers is covered by a tube sealingly passed through the wall of the vacuum chamber.

BRIEF DESCRIPTION OF THE DRAWINGS

These and other objects and advantages of the present invention will be better understood from the following description, with reference to the accompanying drawings, in which:

FIGS. 9A to 9E are views showing simulations of the multi-reflection of laser beam wherein the concave and convex reflectors and the laser source are arranged so that the ideal requirements for the multi-reflection are not met, in yet another aspect;

FIGS. 18A and 18B are graphs showing a waveform of a detected pulse deriving from light scattered due to a presence of particles in the He—Ne laser beam curtain;

FIGS. 19A and 19B are graphs showing a waveform of a detected pulse deriving from light scattered due to a presence of particles in the semiconductor laser beam curtain (common coherence length of more than 10 m);

FIGS. 20A and 20B are graphs showing a waveform of a detected pulse deriving from light scattered due to a presence of particles in the semiconductor laser beam curtain (coherence length of 1 mm);

FIG. 21E is a graph showing a light intensity of the introduced laser beam prior to being reflected between the concave and convex reflectors;

DESCRIPTION OF THE PREFERRED EMBODIMENTS

Figure 1:
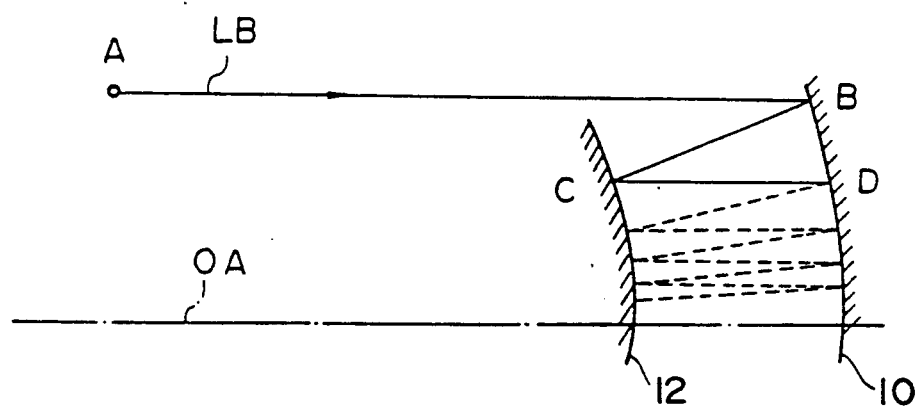
FIG. 1 is a schematic view showing an arrangement of concave and convex reflectors for explaining the principle of the present invention.

In FIG. 1, which shows the principle of the present invention, concave and convex reflectors 10 and 12 having spherical or cylindrical shape reflecting surfaces are spaced apart so that a predetermined constant distance is maintained between the concave and convex reflecting surfaces thereof, in such a manner that the two centers of curvature thereof are aligned with each other on a common optical axis OA shown by a chain line.

As shown in FIG. 1, a laser beam LB, which is emitted from a laser source (such as a semiconductor laser device disposed at a point A) in parallel with the optical axis OA, is introduced between the concave and convex reflectors 10 and 12 so that it is first reflected at a point B by the concave reflector 10 and is then reflected at a point C by the convex reflector 12. The laser beam reflected at the point C is again reflected at a point D by the concave reflector 10. Assuming that the concave and convex reflectors 10 and 12 can be arranged so that the introduced beam segment AB is in parallel with the second reflected beam segment CD, in theory the laser beam is permanently reflected between the concave and convex reflectors 10 and 12 in such a manner that the beam converges on the optical axis OA. This is because, when the beam segments reflected at each of the even number of reflections between the concave and convex reflectors 10 and 12 (namely, all of the beam segments reflected from the convex reflector 12 toward the concave reflector 10) are in parallel with the optical axis OA, the beam segments reflected at each of the odd number of reflections between the concave and convex reflectors 10 and 12 are advanced toward a mid point of a segment of the optical axis OA between the concave reflector 10 and the center $O_1$ thereof. Accordingly, the laser beam LB can be multi-reflected between the concave and convex reflectors 10 and 12 toward the optical axis OA in such a manner that a pitch of the multi-reflected beam segments gradually becomes closer toward the optical axis OA, thereby obtaining a laser beam curtain in which the multi-reflected beam segments are overlapped with respect to each other so that a light intensity thereof is greatly enhanced.

The requirements for the multi-reflection of a laser beam as mentioned above will be explained below with reference to FIG. 2.

Figure 2:
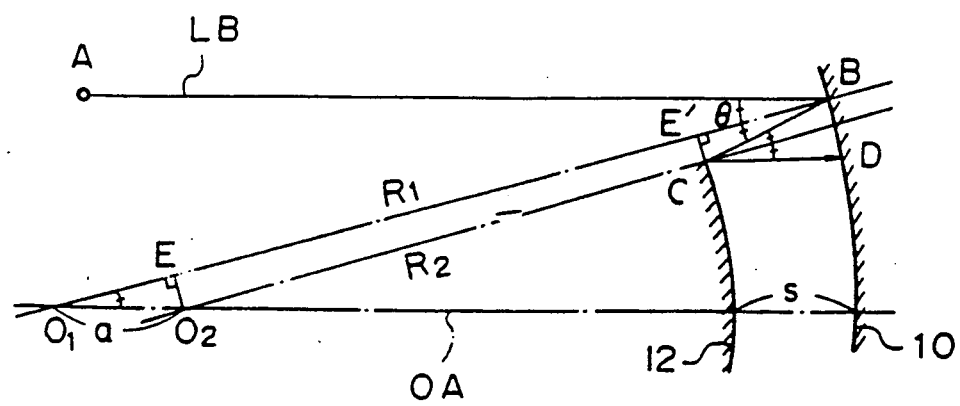
FIG. 2 is a schematic view showing an arrangement of the concave and convex reflectors for explaining ideal requirements for causing a multi-reflection of laser beam according to the present invention.

In FIG. 2, the concave and convex reflectors 10 and 12 have centers of curvature $O_1$ and $O_2$, respectively, which are aligned with each other on the optical axis OA. Symbols $R_1$ and $R_2$ designate the radii of curvature of the concave and convex reflectors 10 and 12, which are equivalent to segments $BO_1$ and $CO_2$ of two chain lines passing through the points B and $O_1$ and the points C and $O_2$, respectively, as shown in FIG. 2. Symbols E and E' designate two points at which the segment $BO_1$ intersects a perpendicular line drawn from the center $O_2$ and the point C thereto, respectively. Symbols a and s designate a distance between the centers of curvature $O_1$ and $O_2$ and a distance measured between the concave and convex reflectors 10 and 12 along the optical axis OA, respectively.

To establish the parallel relationship between the introduced beam segment AB and the second reflected beam segment CD, the radii $R_1$ and $R_2$ forming normal lines with respect to the points B and C must be in parallel to each other. Under these conditions, $$\angle EO_1O_2 = \angle E'BC, \ EO_2 = E'C$$

$$\triangle EO_1O_2 \equiv \triangle E'BC.$$

$$\therefore BC = O_1O_2 = a$$

Where the center $O_2$ is the origin of the rectangular coordinates, the original axis OA forms the abscissa thereof, and where $\angle ABO_1 = \theta$, the points B and C are represented as follows:

$B: (R_1\cos\theta; \ R_1\sin\theta)$
$C: (a + R_2\cos\theta; \ R_2\sin\theta)$ $$\begin{aligned}
\therefore (BC)^2 &= (R_1\cos\theta - (a + R_2\cos\theta))^2 + (R_1\sin\theta - R_2\sin\theta))^2 \\
&= ((R_1 - R_2)\cos\theta - a)^2 + (R_2 - R_2)^2\sin^2\theta \\
&= (R_1 - R_2)^2 - 2a(R_1 - R_2)\cos\theta + a^2
\end{aligned}$$

Since $(BC)^2 = a^2$, the above formula is reformed as follows:

$$(R_1 - R_2)^2 - 2a(R_1 - R_2)\cos\theta = 0$$

$$\therefore a = (R_1 - R_2)/2\cos\theta$$

Since the space between the concave and convex reflectors 10 and 12 is represented by the distance s, as defined above, $$s = R_1 - R_2 - a = (R_1 - R_2)(1 - \tfrac{1}{2}\cos\theta)$$

$$\therefore a/s = 1/(2\cos\theta - 1) \qquad (1)$$

Therefore, this formula (1) shows the requirements for the multi-reflection of a laser beam (i.e. for establishing a parallel relationship between the introduced beam segment AB and the second reflected beam segment (CD).

If $\theta \approx 0$, a/s is approximately equal to 1. Therefore, the formula e,crc/1/ may be approximately represented as follows:

$$a = s = (R_1 - R_2)/2 \quad (2)$$

Accordingly, when the angle $\theta$ is very small, the formula (2) can be substituted for the formula (1). For example, if $\theta = 2°$, the ratio of a to s is calculated from the formula (1), as follows:

$$a/s = 1.0012$$

This ratio may be regarded as $a/s = 1$ because the difference of 0.12% is negligible.

Therefore, under the conditions that the angle $\theta$ is very small, and that the radius $R_1$ is larger than the radius $R_2$ ($R_1 > R_2$), the optical arrangement of the concave and convex reflectors 10 and 12 and the laser source (the point A) for obtaining a multi-reflection of the laser beam as mentioned above can be carried out by only two factors: to space the concave and convex reflectors 10 and 12 apart by the distance $(R_1 - R_2)/2$ so that the centers of curvature $O_1$ and $O_2$ thereof are aligned with each other on the optical axis OA; or to dispose the laser source (the point A) so that the laser beam is emitted therefrom to the concave reflector 10 substantially in parallel with the optical axis OA.

In the description mentioned above, although the laser beam is first reflected by the concave reflector, it may be first reflected by the convex reflector in such a manner that the laser beam strikes the point C in the direction of the segment BC.

Figure 3A:
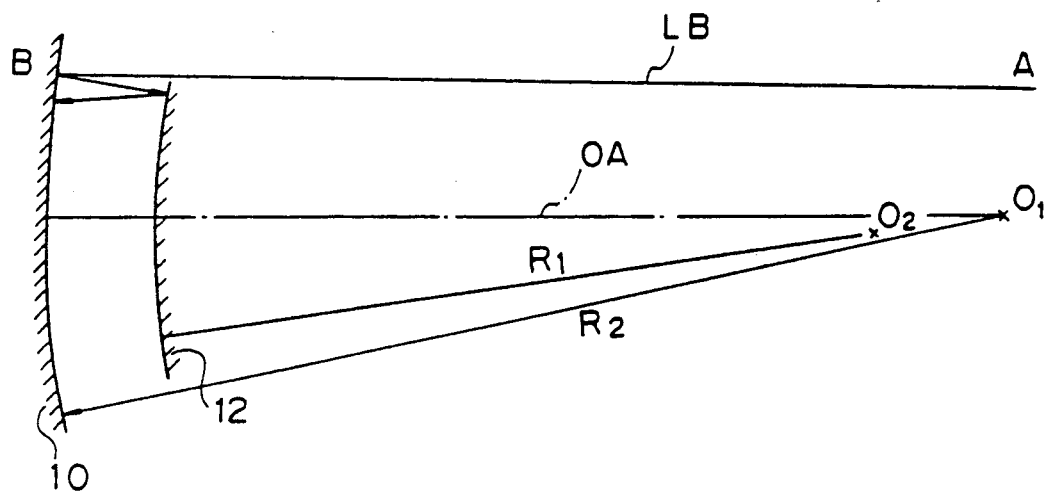
FIGS. 3A and 3B are views showing an arrangement of the concave and convex reflectors for explaining an optical adjustment of a relative position between concave and convex reflectors, FIG. 3B being a perspective view thereof.

It is very difficult to mechanically and permanently fix the concave and convex reflectors 10 and 12 on a suitable frame (not shown in FIGS. 1 and 2), and thus ensure the optical arrangement of the concave and convex reflectors 10 and 12 necessary for obtaining a multi-reflection of the laser beam concerned. For this reason, the concave and convex reflectors 10 and 12 must be mounted on the frame in such a manner that a relative optical positioning therebetween can be minutely adjusted to obtain the multi-reflection of the laser beam concerned.

Where the concave and convex reflectors 10 and 12 have spherical concave and convex reflecting surfaces, if the laser source (the point A) is previously positioned in place with respect to one of the concave and convex reflectors 10 and 12, it is possible to advantageously adjust the other reflector with respect to said one reflector without the need for a cumbersome angular adjustment of the other reflector to obtain the multi-reflection of the laser beam concerned. With reference to FIGS. 3A and 3B and FIGS. 4A to 4C, as examples, an optical adjustment of the concave and convex reflectors 10 and 12 will be explained in detail below:

In FIG. 3A, the laser source (the point A) is positioned with respect to the concave reflector 10 so that the laser beam LB is emitted from the laser source substantially in parallel with the optical axis OA defined by the concave reflector 10, whereas the convex reflector 12 is spaced from the concave reflector 10 by the distance $(R_1 - R_2)/2$, but the center of curvature $O_2$ of the convex reflector 12 is offset from the center of curvature $O_1$ of the concave reflector 10, and thus the center $O_2$ is not on the optical axis OA. In the example shown in FIG. 3A, the convex reflector 12 can be shifted in two directions X and Y (FIG. 3B), which are perpendicular to each other and to the beam segment AB, and accordingly the optical axis OA, whereby the convex reflector 12 can be adjusted so that the center $O_2$ is aligned with the center $O_1$ on the optical axis OA.

Figure 3B:
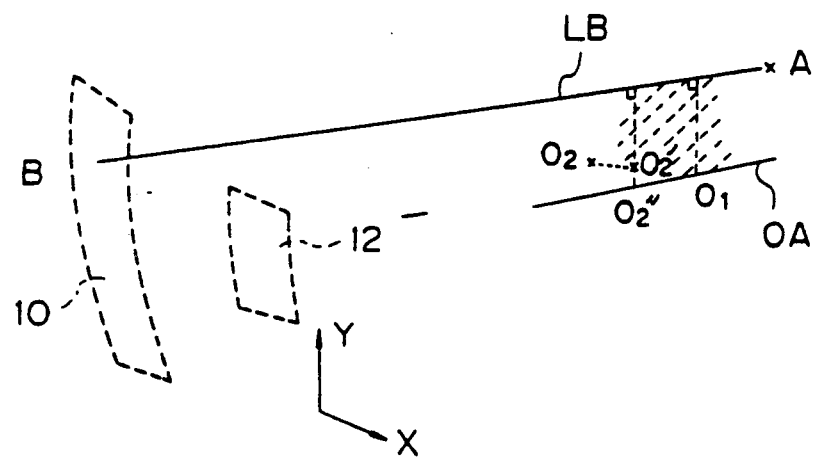
Figure 4A:
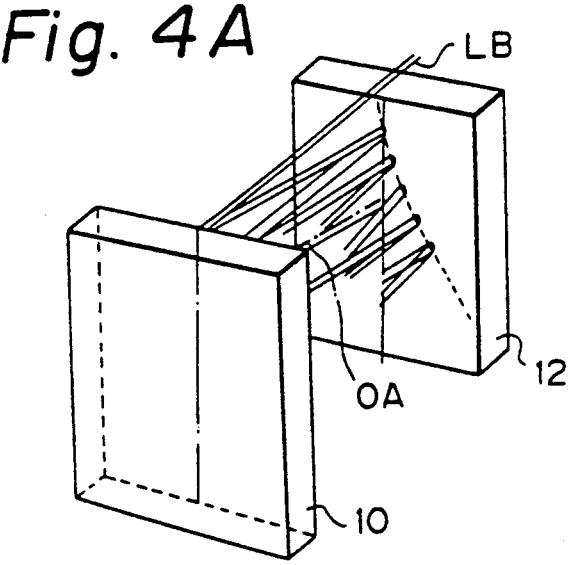
FIGS. 4A to 4C are perspective views showing that the multi-reflected beam segments behave distinctively during the adjustment of FIGS. 3A and 3B.
Figure 4B:
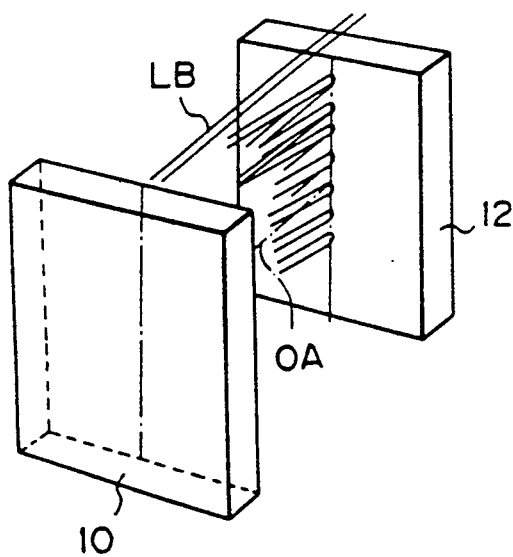
Figure 4C:
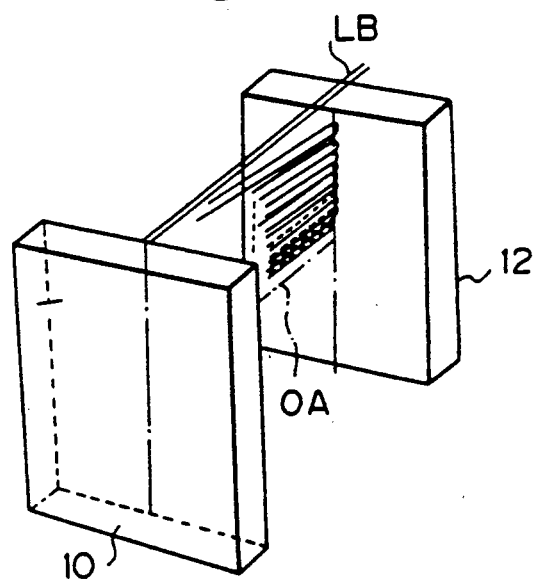

To bring the center $O_2$ into alignment with the center $O_1$ on the optical axis OA, the convex reflector 10 is shifted in the direction X so that the center $O_2$ is positioned in a plane (shown by a hatched area in FIG. 3B) defined by the beam segment AB and the optical axis (the center $O_2$ positioned in the plane is designated by a symbol $O_2'$ in FIG. 3B), and then the convex reflector 12 is shifted in the direction Y so that the center $O_2'$ is positioned on the optical axis OA (the center $O_2'$ positioned on the optical axis OA is designated by a symbol $O_2''$ in FIG. 3B). This adjustment can be visually carried out as shown in FIGS. 4A to 4C. Particularly, when the center $O_2$ is offset from the hatched area (FIG. 3B), the multi-reflected beam segments from a curved plane (FIG. 4A). When the center $O_2$ is positioned at $O_2'$ in the hatched area, the multi-reflected beam segments form a vertical plane (FIG. 4B). When the center $O_2$ is positioned at $O_2''$, so as to be brought into alignment with the centers $O_1$ on the optical axis OA, the multi-reflected beam segments not only form a vertical plane, but also provide the desired laser beam curtain, as mentioned hereinbefore, having an enhanced light intensity in the zone around the optical axis OA. As apparent from FIGS. 4A to 4C, since the multi-reflected laser beam segments behave distinctively when the center $O_2$ is positioned at the singular point ($O_2'$, $O_2''$), the center $O_2$ can be easily aligned with the centers $O_1$ on the optical axis OA by a visual adjustment of the convex reflector 12.

Note, although the convex reflector 12 is adjusted in relation to the concave reflector 10 in the example shown in FIGS. 3A and 3B, the concave reflector 10 may be adjusted in relation to the convex reflector 12, and the laser source (the point A) positioned with respect to the convex reflector 12 so that the laser beam LB is emitted from the laser source substantially in parallel with the optical axis OA defined by the convex reflector 12.

Where the concave and convex reflectors have cylindrical concave and convex reflecting surfaces, an angular adjustment is involved in the relative optical positioning of the concave and convex reflectors to obtain the multi-reflection of a laser beam concerned, so that the longitudinal axes of the cylindrical surfaces, each of which perpendicularly intersects the generatrix of the corresponding cylindrical surface, are in parallel with each other. Note, it is possible to obtain a laser beam curtain in which the multi-reflected beam segments are overlapped with respect to each other at a much closer pitch, so that a light intensity thereof is greatly enhanced.

Figure 5A:
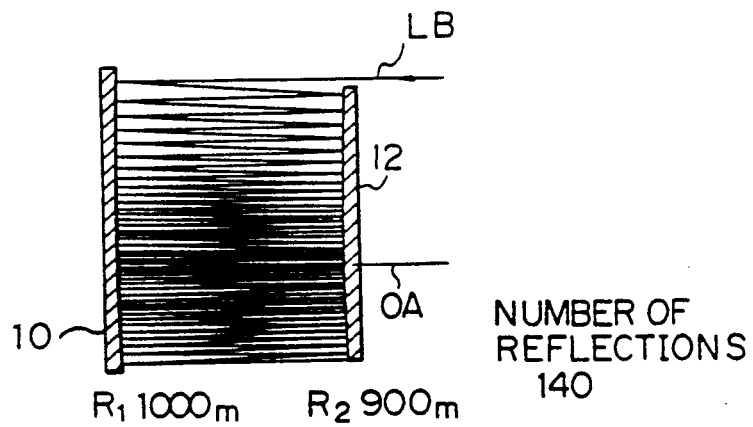
FIGS. 5A to 5C are views showing simulations of the multi-reflection of laser beam wherein the concave and convex reflectors and the laser source are arranged so that the ideal requirements for the multi-reflection are met.
Figure 5B:
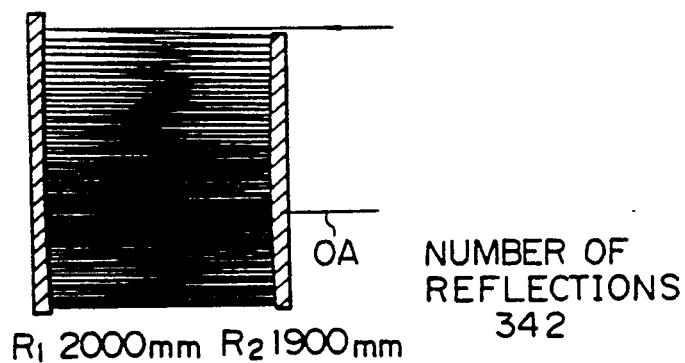
Figure 5C:
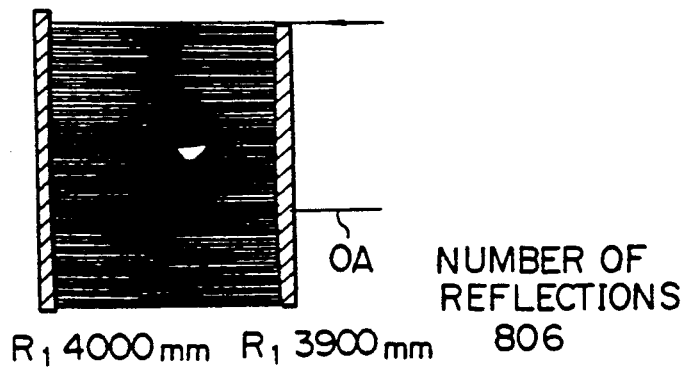

FIGS. 5A, 5B and 5C show simulations of the multi-reflection of a laser beam, wherein the concave and convex reflectors 10 and 12 and the laser source are arranged so that the ideal requirements according to the above-mentioned formula (1) can be met. In FIG. 5A, the concave and convex reflectors 10 and 12 have radii of 1000 mm, and 900 mm, respectively; in FIG. 5B, the concave and convex reflectors 10 and 12 have radii of 2000 mm and 1900 mm, respectively; and in FIG. 5C, the concave and convex reflectors 10 and 12 have radii of 4000 mm and 3900 mm, respectively. In all of the simulations since a between the radii of the concave and convex reflectors 10 and 12 is 100 mm, the distance s therebetween is set at 50 mm. In FIGS. 5A, 5B, and 5C, the laser beam is introduced between the concave and convex reflectors 10 and 12 in parallel with the optical axis OA. In all of the simulations, since a distance s between the laser beam and the optical axis OA is 50 mm, the angle $\theta$ is equal to about 2.5° (50/1000 rad) in FIG. 5A; to about 1.25° (50/2000 rad) in FIG. 5B; and to about 0.625° (50/4000 rad) in FIG. 5C.

In the simulation of FIG. 5A, the laser beam was multi-reflected 140 times; in the simulation of FIG. 5B, the laser beam was multi-reflected 342 times; and in the simulation of FIG. 5B, the laser beam was multi-reflected 806 times. As seen from the simulations the smaller the angle $\theta$, the greater the number of times the laser beam is reflected between the concave and convex reflectors. Note, in the simulations of FIGS. 5A, 5B, and 5C, the laser beam was multi-reflected between the concave and convex reflectors by passing through the optical axis OA and thus was emitted from the space between the concave and convex reflectors at a side opposite to the side having the space through which the laser beam was introduced, but the laser beam is multi-reflected at much closer pitch in the zone around the optical axis OA.

FIGS. 6A, 6B, 6C and 6D show simulations of the multi-reflection of a laser beam wherein the concave and convex reflectors 10 and 12 and the laser source are arranged so that the ideal requirements according to the formula e,crc/1/ are not met.

Figure 6A:
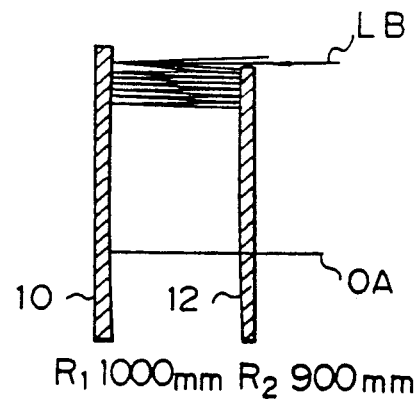
FIGS. 6A to 6D are views showing simulations of the multi-reflection of laser beam wherein the concave and convex reflectors and the laser source are arranged so that the ideal requirements for the multi-reflection are not met, in one aspect.

The simulation of FIG. 6A was performed under the same condition as in FIG. 5A except that the distance s between the concave and convex reflectors was set at 30 mm instead of 50 mm. As shown in FIG. 6A, the laser beam was multi-reflected at a relatively wide pitch between the concave and convex reflectors at the side of the space therebetween through which the laser beam was introduced, and was then emitted from the same side.

Figure 6B:
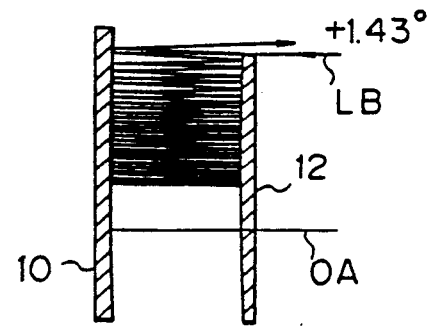

The simulation of FIG. 6B was performed under the same conditions as in FIG. 6A, except that the laser beam was not introduced between the concave and convex reflectors in parallel with the optical axis OA but at an angle of +1.43° with respect to the parallel laser beam shown in FIG. 6A. Note that an angle measured in the clockwise direction from the horizontal line (i.e., the parallel laser beam shown in FIG. 6A) is defined as a positive angle, and an angle measured in the counter-clockwise direction from the horizontal line is defined as a negative angle. Similar to FIG. 6A, in FIG. 6B the laser beam was multi-reflected between the concave and convex reflectors at the laser beam introduction side, and then emitted from the same side. Nevertheless, as apparent from FIG. 6B, the laser beam was multi-reflected at a much closer pitch at the side of the optical axis OA.

Figure 6C:
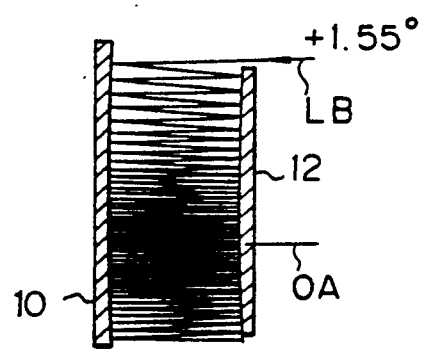

The simulation of FIG. 6C was performed under the same conditions as in FIG. 6A, except that the laser beam was introduced between the concave and convex reflectors at an angle of +1.55° with respect to the parallel laser beam shown in FIG. 6A. In FIG. 6C, the laser beam was multi-reflected between the concave and convex reflectors by passing through the optical axis OA and thus was emitted from the space between the concave and convex reflectors at the side opposite to the laser beam introduction side, but the laser beam was multi-reflected at a much closer pitch in the zone around the optical axis OA.

Figure 6D:
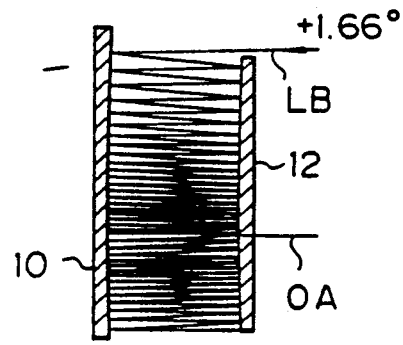

The simulation of FIG. 6D was performed under the same conditions as in FIG. 6A, except that the laser beam was introduced between concave and convex reflectors at an angle of +1.66° with respect to the parallel laser beam shown in FIG. 6A. In FIG. 6D, the laser beam was multi-reflected between the concave and convex reflectors by passing through the optical axis OA, and thus was emitted from the space between the concave and convex reflectors at the side opposite to the laser beam introduction side, but the laser beam was multi-reflected at a relatively closer pitch in the zone around the optical axis OA.

FIGS. 7A, 7B, 7C, 7D, and 7E also show simulations of the multi-reflection of a laser beam, wherein the concave and convex reflectors 10 and 12 and the laser source are arranged so that the ideal requirements according to the formula ① are not met.

Figure 7A:
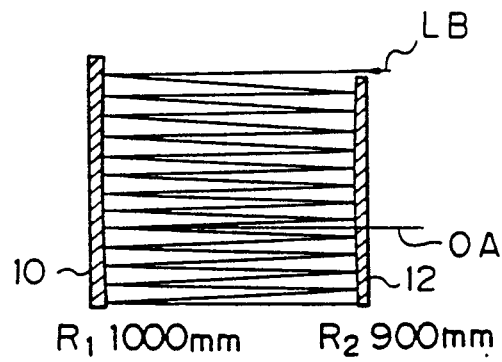
FIGS. 7A to 7E are views showing simulations of the multi-reflection of laser beam wherein the concave and convex reflectors and the laser source are arranged so that the ideal requirements for the multi-reflection are not met, in another aspect.

The simulation of FIG. 7A was performed under the same conditions as in FIG. 5A, except that the distance s between the concave and convex reflectors was set at 70 mm instead of 50 mm. As shown in FIG. 7A, the laser beam was multi-reflected at a relatively wide pitch between the concave and convex reflectors by passing through the optical axis OA, and thus was emitted from the space between the concave and convex reflectors at the side opposite to the laser beam introduction side.

Figure 7B:
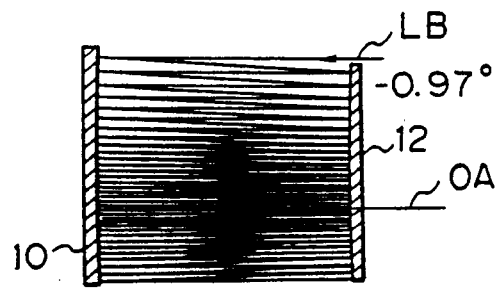

The simulation of FIG. 7B was performed under the same conditions as in FIG. 7A, except that the laser beam was not introduced between the concave and convex reflectors in parallel with the optical axis OA but at an angle of −0.97° with respect to the parallel laser beam shown in FIG. 7A. As shown in FIG. 7B, the laser beam was multi-reflected at a relatively close pitch between the concave and convex reflectors by passing through the optical axis OA, and thus was emitted from the space between the concave and convex reflectors at the side opposite to the laser beam introduction side.

Figure 7C:
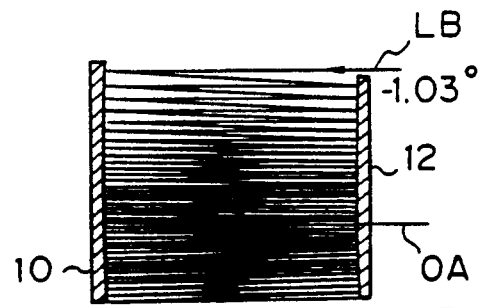

The simulation of FIG. 7C was performed under the same conditions as in FIG. 7A, except that the laser beam was introduced between the concave and convex reflectors at an angle of −1.03° with respect to the parallel laser bean shown in FIG. 7A. In FIG. 7C, the laser beam was multi-reflected in much the same manner as in FIG. 7B.

Figure 7D:
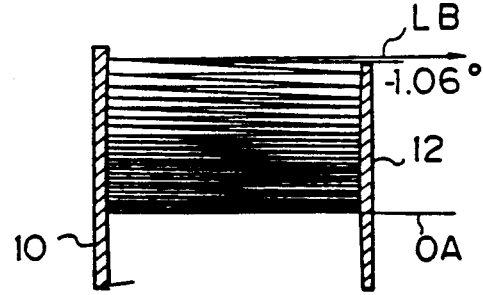

The simulation of FIG. 7D was performed under the same conditions as in FIG. 7A, except that the laser beam was introduced between the concave and convex reflectors at an angle of −1.06° with respect to the parallel laser beam shown in FIG. 7A. In FIG. 7D, the laser beam was multi-reflected between the concave and convex reflectors until reaching the optical axis OA, and then was emitted from the laser beam introduction side. Nevertheless, the laser beam was multi-reflected at a much closer pitch in the zone around the optical axis OA.

Figure 7E:
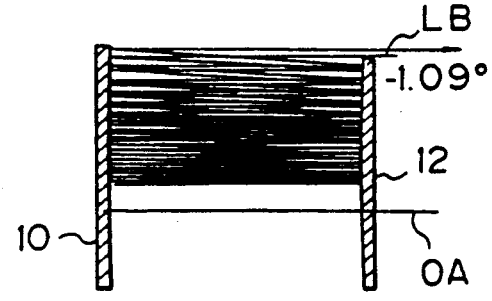

The simulation of FIG. 7E was performed under the same conditions as in FIG. 7A, except that the laser beam was introduced between the concave and convex reflector at an angle of −1.09° with respect to the parallel laser beam shown in FIG. 7A. In FIG. 7E, the laser beam was multi-reflected between the concave and convex reflectors in the laser beam introduction side, and then emitted from the same side. Nevertheless, the laser beam was multi-reflected at a much closer pitch at the side of the optical axis.

As seen from FIGS. 6A to 6D and FIGS. 7A to 7E, although the concave and convex reflectors and the laser source are arranged so that the ideal requirements according to the formula ① are not met, a zone in which the laser beam is multi-reflected at a much closer pitch can be obtained by adjusting an angle of incidence of the laser beam to be introduced between the concave and convex reflectors. Namely, the multi-reflection of the laser beam concerned can be obtained by suitably arranging the concave and convex reflectors and the laser source, regardless of the ideal requirements of formula ①.

Therefore, although the arrangement of the concave and convex reflectors and the laser source does not meet the ideal requirements of formula ①, this is also within the scope of the present invention as long as the multi-reflection of the laser beam concerned can be obtained.

As mentioned with reference to FIGS. 5A to 5C, when the concave and convex reflectors and the laser source are arranged so that the ideal requirements of the formula ① are met, the multi-reflection of a laser beam can be obtained. But, in practice, it is difficult to obtain an arrangement of the concave and convex reflectors and the laser source which meets the ideal requirements of formula ①, because the positioning tolerance as well as the tolerance of the radii of curvature of the reflectors 10 and 12 must be taken into consideration.

In particular, sometimes the parallel relationship between the laser beam and the optical axis cannot be established.

Note, obviously when the laser beam is not in parallel with the optical axis, a multi-reflection of a laser beam concerned cannot be obtained under the ideal requirements of the formula ①. Nevertheless, it is possible to obtain the multi-reflection of a laser beam concerned even if the laser beam is not in parallel with the optical axis as mentioned hereinafter.

Figure 8:
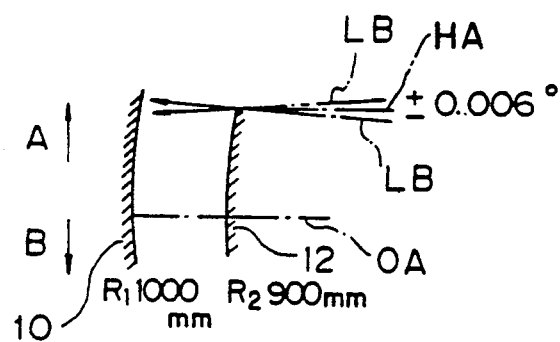
FIG. 8 is an view showing that the laser beam strikes the concave reflector at an angle of deviation of ±0.006°.

According to the present invention, it is possible to compensate the non-parallel relationship between the laser beam and the optical axis by moving the concave reflector perpendicular to the optical axis. For example, as shown in FIG. 8, when the laser beam has an angle of deviation of +0.006° with respect to a horizontal axis HA which is in parallel with the optical axis OA, this deviation angle can be compensated by moving the concave reflector in one of the opposite directions shown by arrows A and B, whereby the multi-reflection of the laser beam concerned can be obtained. This compensation will be explained in detail with reference to FIGS. 9A to 9D and FIGS. 10A and 10D.

Figure 9A:
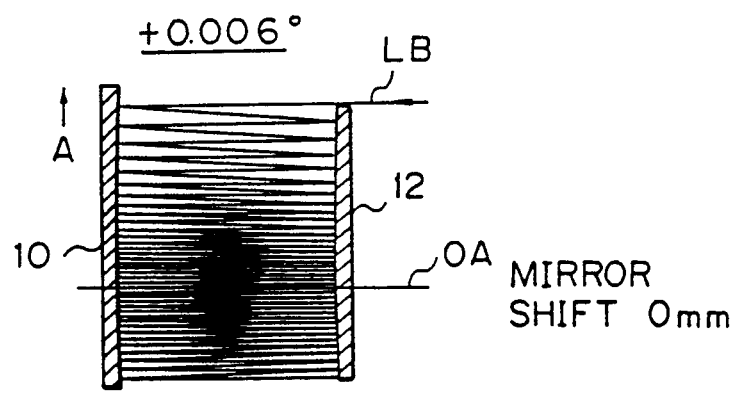
Figure 9B:
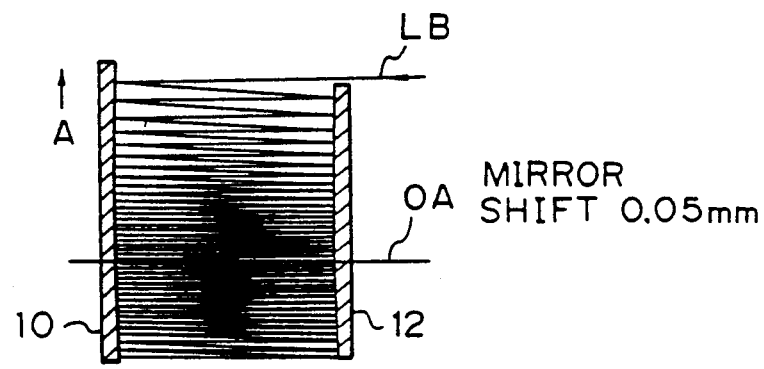
Figure 9C:
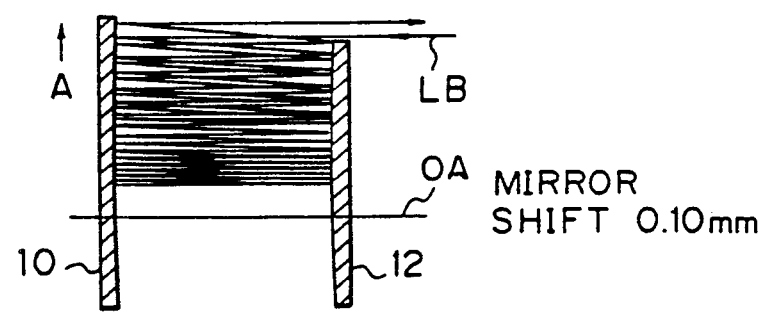
Figure 9D:
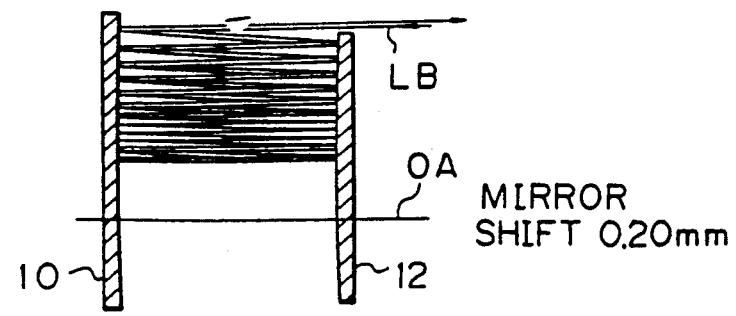

FIGS. 9A to 9D show simulations of the multi-reflection of a laser beam wherein the concave and convex reflectors 10 and 12 are arranged as in FIG. 5A, but the laser beam has an angle of deviation of −0.006°. In FIG. 9A, the concave reflector 10 is at an initial position, i.e., movement of the concave reflector 10 is zero. In FIG. 9B, the concave reflector 10 is shifted in the direction A by a distance of 0.05 mm; in FIG. 9C, the concave reflector 10 is shifted in the direction A by a distance of 0.10 mm; and in FIG. 9D, the concave reflector 10 is shifted in the direction A by a distance of 0.20 mm.

Figure 10A:
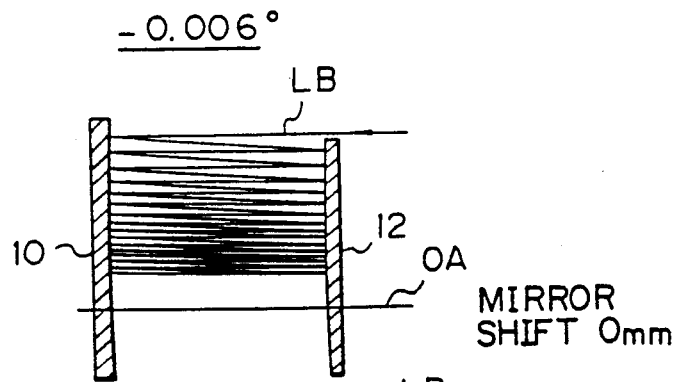
FIGS. 10A to 10D are views showing simulations of the multi-reflection of a laser beam wherein the concave and convex reflectors and the laser source are arranged so that the ideal requirements for the multi-reflection are not met, in yet a further aspect.
Figure 10B:
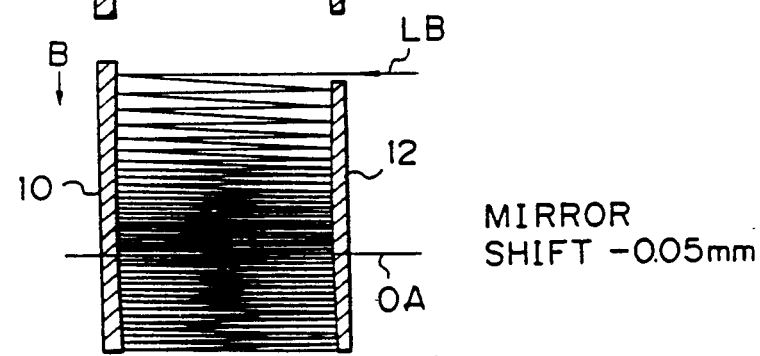
Figure 10C:
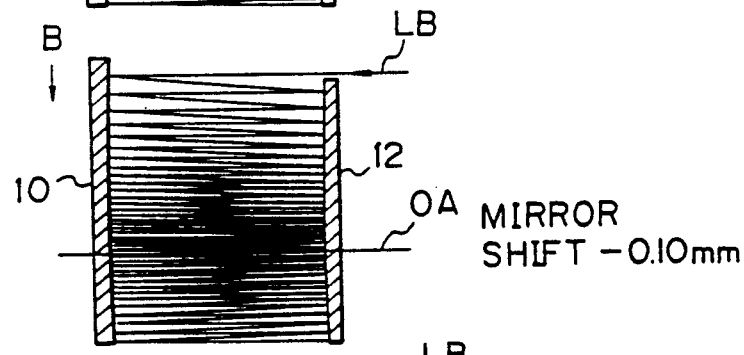
Figure 10D:
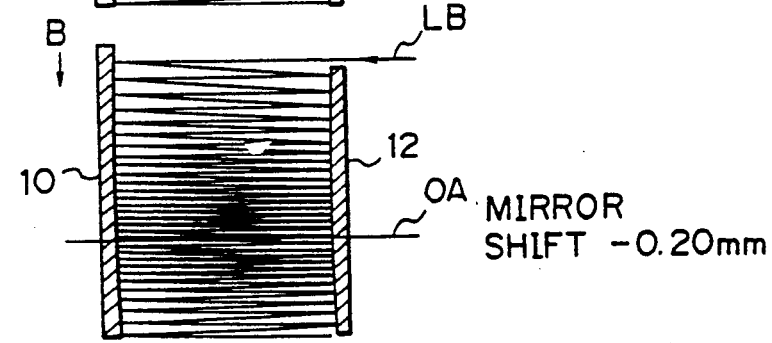
Figure 12A:
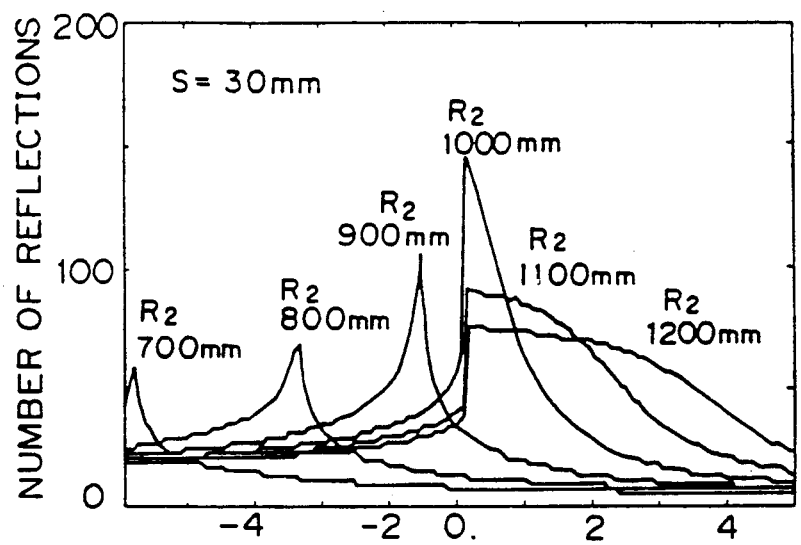
FIGS. 12A to 12E are simulations of the multi-reflections of a laser beam obtained when the radius of curvature of the convex reflector and the distance between the concave and convex reflectors are varied within the predetermined range in FIG. 11
Figure 12B:
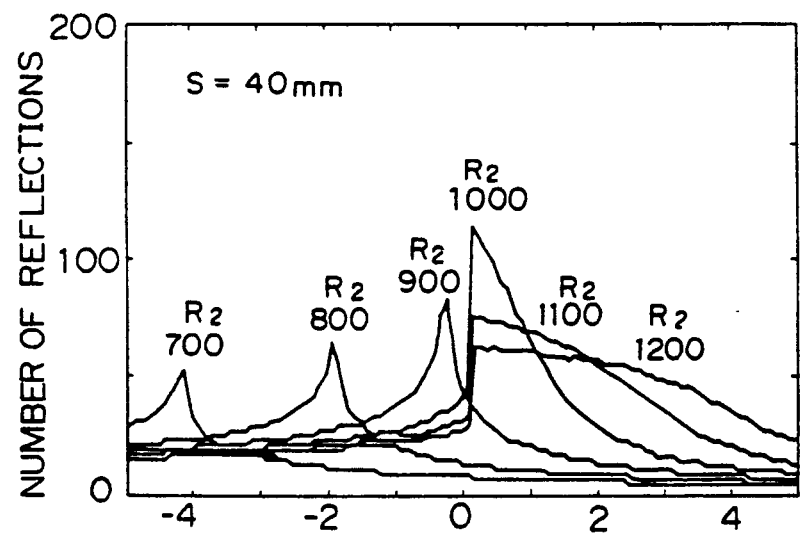
Figure 12C:
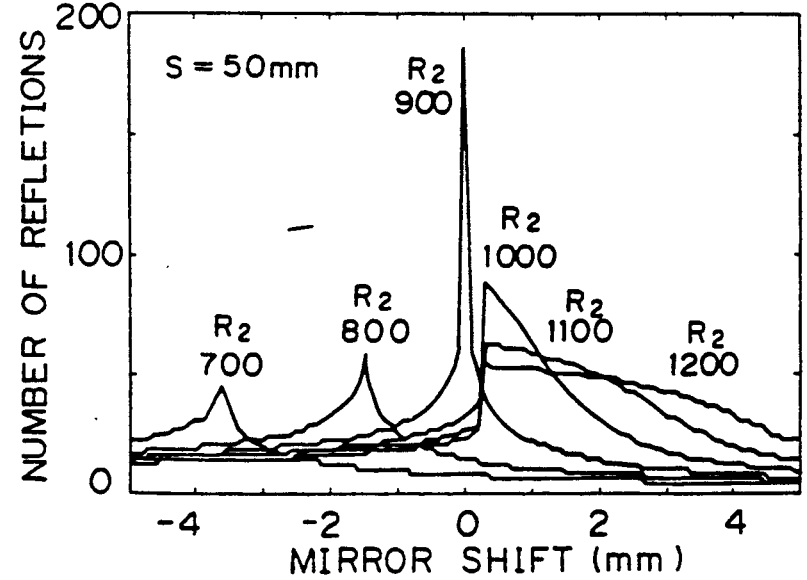
Figure 12D:
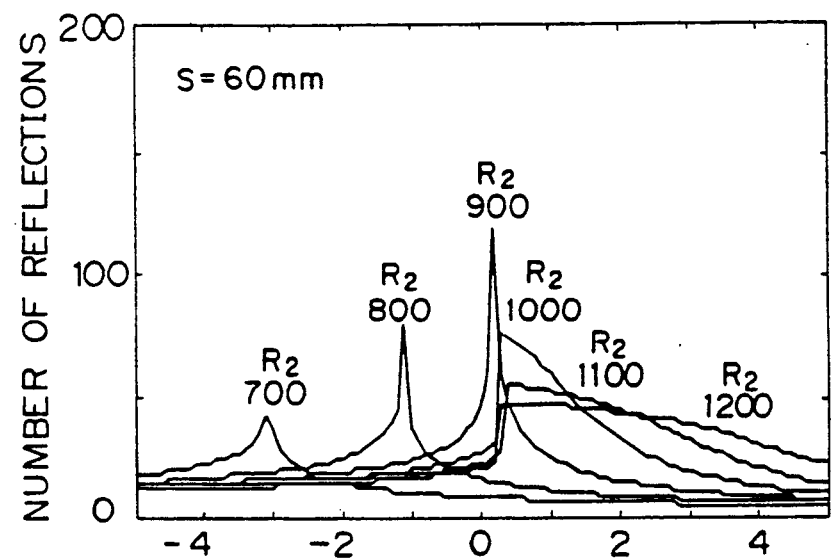
Figure 12E:
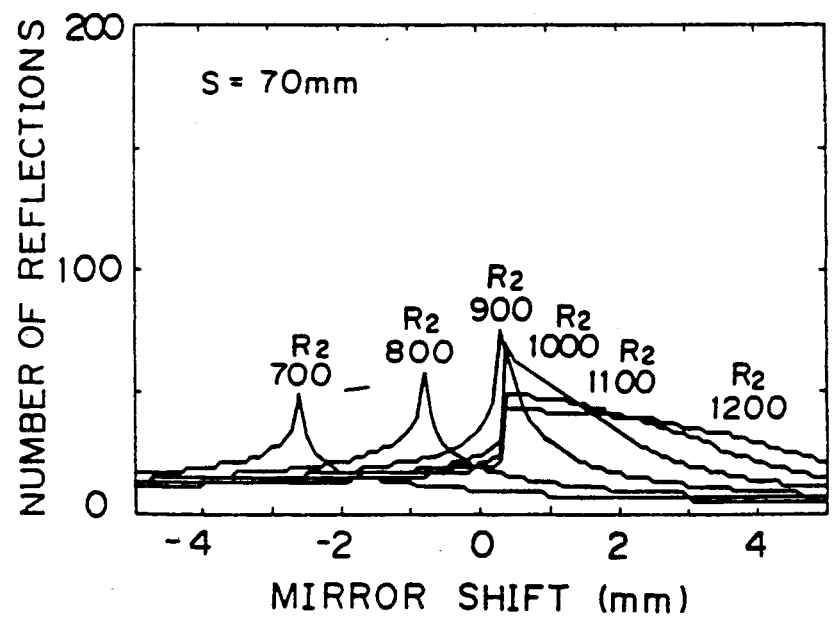

FIGS. 10A to 10D also show simulations of the multi-reflection of a laser beam wherein the concave and convex reflectors 10 and 12 are arranged as in FIG. 5A but the laser beam has an angle of deviation of +0.006°. In FIG. 10A, the concave reflector 10 is at an initial position, i.e., movement of the concave reflector 10 is zero. In FIG. 10B, the concave reflector 10 is shifted in the direction B by a distance of 0.05 mm; in FIG. 10C, the concave reflector 10 is shifted in the direction B by a distance of 0.10 mm; and in FIG. 10D, the concave reflector 10 is shifted in the direction B by a distance of 0.20 mm.

As seen from FIGS. 9A to 9D and FIGS. 10A to 10D, although the laser beam has an angle of deviation of ±0.006°, the multi-reflection of the laser beam concerned can be obtained by moving the concave reflector 10 by a distance of 0.05 mm in the directions A and B, respectively.

Figure 11:
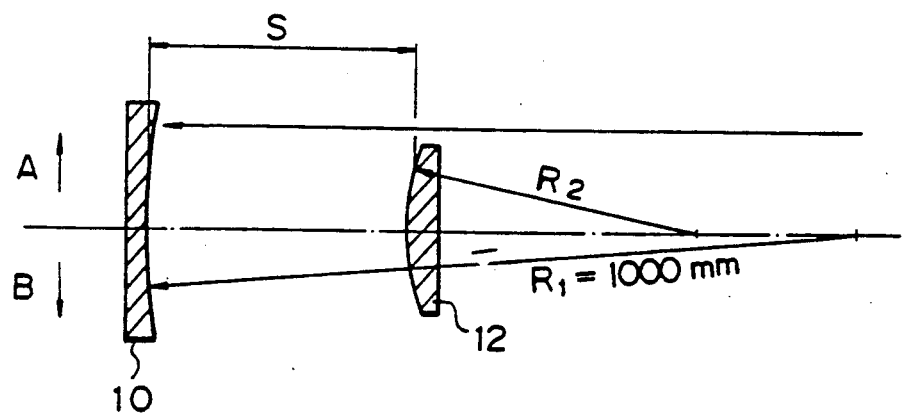
FIG. 11 is a schematic view showing an arrangement of the concave and convex reflectors wherein the radius of curvature of the convex reflector and the distance between the concave and convex reflectors are varied within a predetermined range.

Furthermore, according to the present invention, although the parameters $R_1$, $R_2$ and s are varied within a relative wide range with respect to each other, it is possible to obtain a multi-reflection of the laser beam concerned by the movement of the concave reflector. This can be also shown by a simulation. For example, in an arrangement as shown in FIG. 11, when the radius $R_2$ of the convex reflector 12 is varied from 700 mm to 1200 mm by increments of 100 mm, the radius $R_1$ of the concave reflector 10 is fixed, when the distance s between the concave and convex reflectors 10 and 12 is varied from 30 mm to 70 m by increments of 10 mm, and the laser beam is introduced between the concave and convex reflectors 10 and 12 in parallel with the optical axis OA, the distance between the laser beam and the optical axis OA being 20 mm, a simulation was obtained of resultant changes in the multi-reflection of a laser. The simulation results are shown in FIGS. 12A to 12E. In FIGS. 12A to 12E, the abscissa shows a movement of the concave reflector 10 wherein an upward shift (arrow A shown in FIG. 11) of the concave reflector 10 is defined as positive and a downward shift (arrow B shown in FIG. 11) thereof is negative, and the ordinate shows a number of reflections of the laser beam.

As seen from FIGS. 12A to 12E, when the requirements of formula ① are met (s=50 mm, $R_2$=900 mm), the shift of the concave reflector=0), the number of reflections of the laser beam is at a maximum. But even if the requirements of formula ① are not met, it is possible to obtain a large number of reflections of the laser beam.

Figure 13:
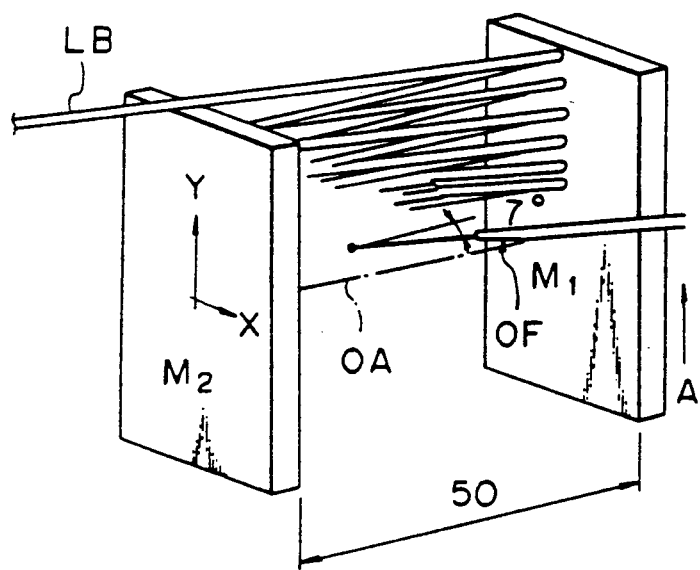
FIGS. 13A is a schematic view showing an arrangement of the concave and convex reflectors which is actually constructed for measuring a distribution of light intensity of a laser beam curtain formed by the multi-reflected beam segments.
FIGS. 13B is a schematic view showing an optical fiber probe for measuring a light intensity of the laser beam curtain.
Figure 13:
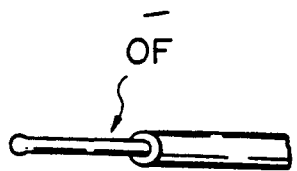

An arrangement for the multi-reflection of the laser beam was actually constructed, as generally shown in FIG. 13A, for measuring a distribution of light intensity of the laser beam curtain formed by the multi-reflected beam segments. In the actual arrangement, the concave and convex reflectors $M_1$ and $M_2$ had radii of 1000 mm and 900 mm, respectively, and the distance s therebetween was a set at 50 mm, and a He—Ne laser beam LB (2 mW) was used. As shown in FIG. 13A, the concave reflector $M_1$ was shifted in a direction shown by an arrow A, for the purpose mentioned hereinafter, and the concave reflector $M_2$ was shifted in the directions shown by arrows X and Y, which are perpendicular to each other and thus the arrangement met the requirements of formula ①. To measure the distribution of light intensity of the laser beam curtain, an optical fiber OF was utilized as a probe. As shown in FIG. 13B, the optical fiber probe OF has a sheath-stripped end having a rounded tip, and another end (not shown) coupled to a light detector such as a photomultiplier tube.

During the measurement, the rounded tip of the optical fiber probe OF was placed in contact with the laser beam curtain at a slight angle of, for example, 7 degrees, as shown in FIG. 13A. A distribution of the light intensity of the laser beam curtain was measured by moving the optical fiber probe OF from the uppermost side of the laser beam curtain toward the optical axis OA, while maintaining the above angle of the optical fiber probe to the laser beam curtain. Note, when the optical fiber prove OF is oriented to the laser beam curtain as shown in FIG. 13A, only a light intensity of the beam segments reflected at the even-number of reflections of the beam is measured, because the beam segments reflected from the convex reflector $M_2$ toward the concave reflector $M_1$ are only intercepted by the rounded tip of the optical fiber probe OF.

Figure 14:
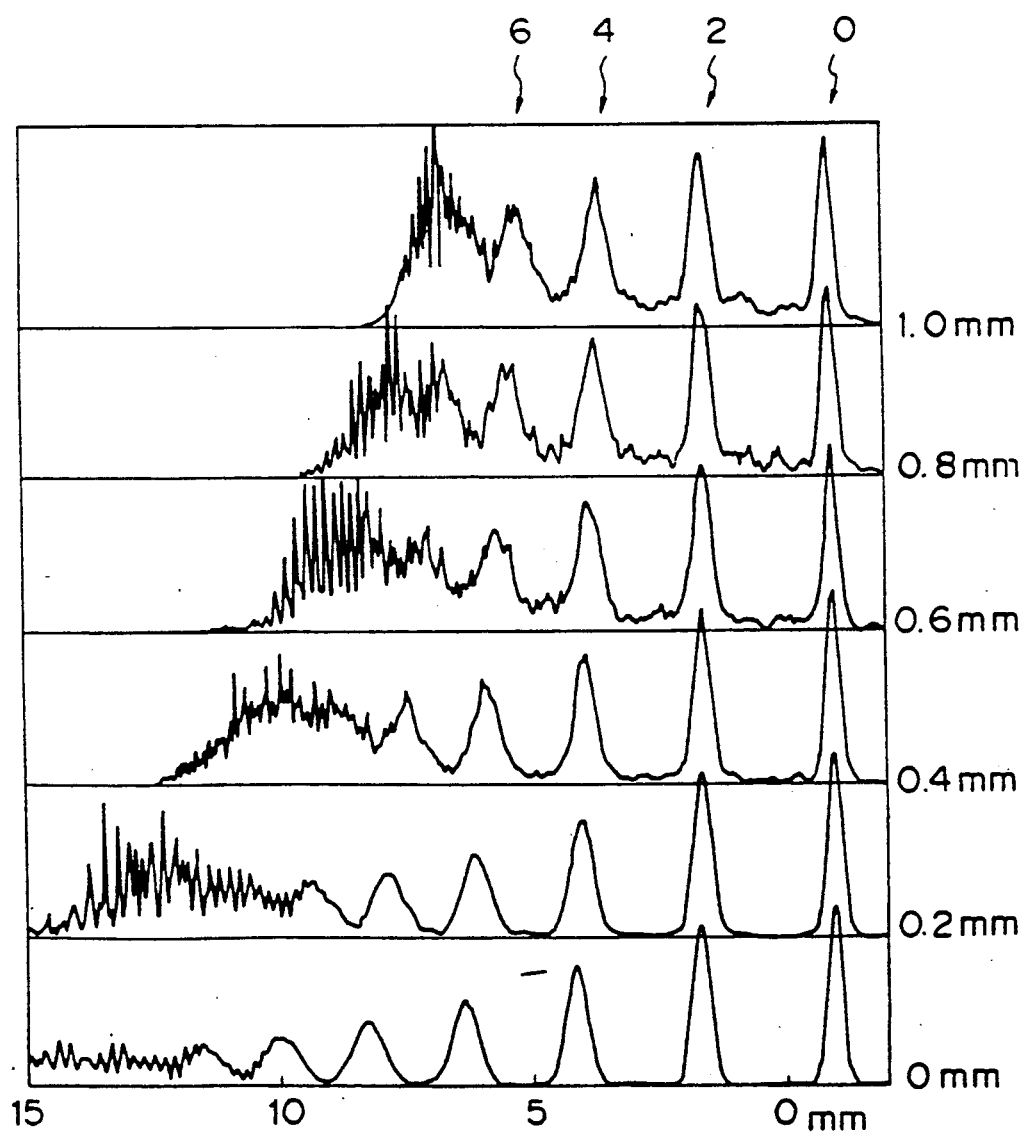
FIG. 14 is a graph showing five characteristics each representing a distribution of light intensity of a He—Ne laser beam curtain measured in a case wherein the concave reflector was shifted in FIG. 13A within a predetermined range.

In each of five cases wherein the concave reflector $M_1$ is not shifted in the direction A (i.e., remains at the initial position); is shifted by a distance of 0.2 mm; by a distance of 0.4 mm; by a distance of 0.6 mm; by a distance of 0.8 mm; and by a distance of 1.0 mm, an actual measurement was performed in the above manner. The results of the measurement are shown in FIG. 14. In FIG. 14, the five characteristics indicated by 0 mm, 0.2 mm, 0.4 mm, 0.6 mm, 0.8 mm, and 1.0 mm correspond to the distributions of light intensity of the laser beam curtains obtained in the above-mentioned five cases, respectively, and the abscissa shows a distance by which the rounded tip of the optical fiber probe OF is moved along each of the five laser beam curtains. In each of the five characteristics, the first peak indicated by "0" represents a light intensity of the introduced or non-reflected laser beam; the second peak indicated by "2" represents a light intensity of the beam segment reflected twice; the third peak indicated by "4" represents a light intensity of the beam segment reflected four times; and the fourth peak indicated by "6" represents a light intensity of the beam segment reflected six times. In each of the characteristics indicated by 1.0 mm, 0.8 mm, and 0.6 mm, the beam segments reflected more than eight times are overlapped with respect to each other so that a light intensity thereof is enhanced, but these beam segments interfere with each other to form an irregular band. In each of the characteristics indicated by 0.4 mm and 0.2 mm, the fifth peak appears and represents a light intensity of the beam segment reflected eight times, but the beam segments reflected more than ten times interfere with each other to form an irregular band. In the characteristics indicated by 0 mm, the fifth and sixth peaks appear and represent light intensities of the beam segments reflected eight and ten times, respectively, but the beam segments reflected more than twelve times interface with each other to form an irregular band.

Figure 15A:
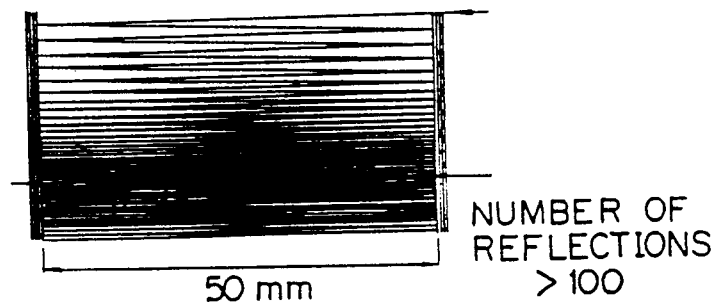
FIGS. 15A to 15F are simulations of the multi-reflection of the laser beam corresponding to the five characteristics of FIG. 14.
Figure 15B:
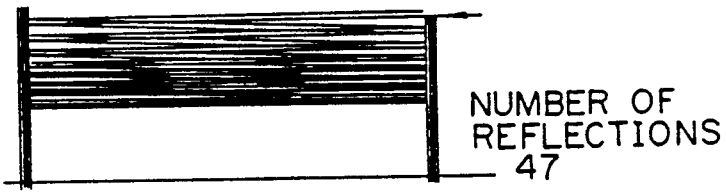
Figure 15C:
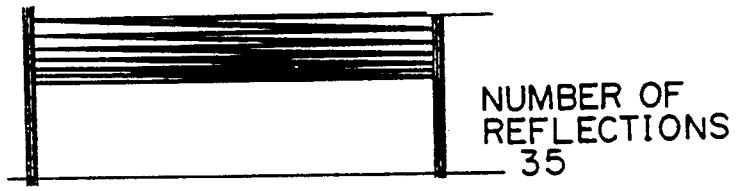
Figure 15D:
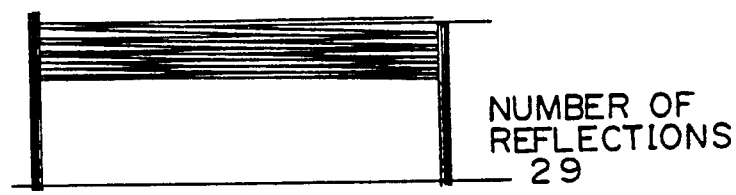
Figure 15E:
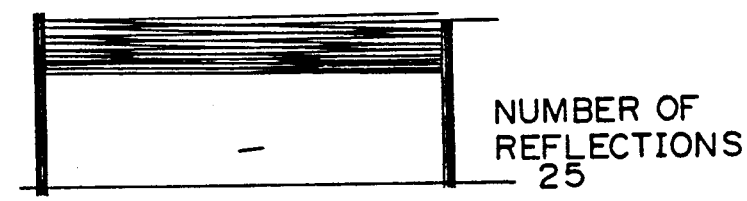
Figure 15F:
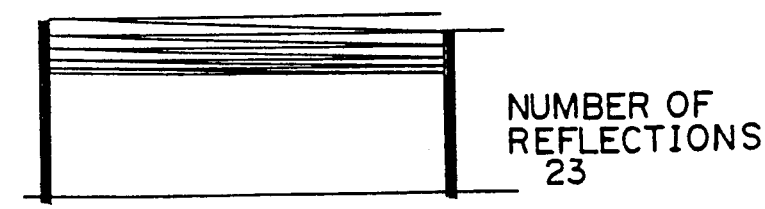

FIGS. 15A to 15F show simulations of the multi-reflections of the laser beam corresponding to the above five characteristics indicated by 0 mm, 0.2 mm, 0.4 mm, 0.6 mm, 0.8 mm, and 1.0 mm. In FIG. 15A, the laser beam was multi-reflected more than 100 times, whereas in FIGS. 15B to 15F, the numbers of reflections are 47, 35, 29, 25, and 23 times, respectively. As apparent from the comparison of the simulations of FIGS. 15A to 15F with the five characteristics of FIG. 14, although the number of reflections of more than 100 times is obtained in FIG. 15A, a light intensity of the irregular band thereof (FIG. 14) in which the reflected beam segments are at a much closer pitch is lower than that of the irregular bands of the other characteristics indicated by 0.2 mm, 0.4 mm, 0.6 mm, 0.8 mm, and 1.0 mm. This is because the reflection loss is large due to the number of reflections of more than 100 times, and because the laser beam is gradually thickened due to an increment of the optical path length thereof. Conversely, in the characteristics indicated by 0.2 mm, 0.4 mm, 0.6 mm, 0.8 mm, and 1.0 mm, each irregular band (i.e. the zone in which the reflected laser beam is returned back to the laser beam introduction side) has a much higher intensity of light than that of the characteristics indicated by 0 mm. Note, in the characteristics indicated by 0.2 mm, 0.4 mm, 0.6 mm, 0.8 mm, and 1.0 mm, each of the irregular bands actually has a higher level of light intensity which is twice that of the corresponding light intensity shown in FIG. 14 because a light intensity of the beam segments reflected at the odd-number of reflections of the beam is not measured.

Accordingly, the irregular bands of the characteristics indicated by 0.2 mm, 0.4 mm, 0.6 mm, 0.8 mm, and 1.0 mm are preferably used as a detection zone for particles rather than the irregular band of the characteristic indicated by 0 mm, to carry out the particle detection with a high probability and a high sensitivity. Especially, the irregular bands of the characteristics indicated by 0.4 mm and 0.6 mm are most suitable as the particle detection zone, because of the width thereof.

As mentioned above, when the He—Ne laser beam is used, the particle detection zone is obtained as the irregular band in which the reflected beam segments interfere with each other. In this detection zone, light scattered due to the presence of particles behaves in a complicated manner due to the affect of the interference of the multi-reflected beam segments. Nevertheless, by using a semiconductor laser beam instead of the He—Ne laser beam, it is possible to eliminate the interference of the multi-reflected beam segments from the detection zone.

Figure 16A:
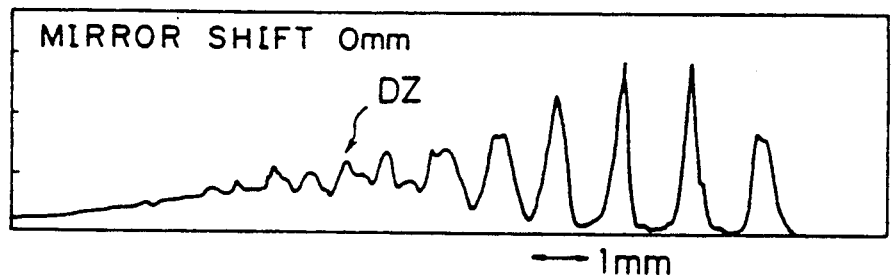
FIGS. 16A to 16C are graphs showing a characteristic representing a distribution of light intensity of a semiconductor laser beam curtain (common coherence length of more than 10 m) wherein the concave reflector was shifted within a predetermined range.
Figure 16B:
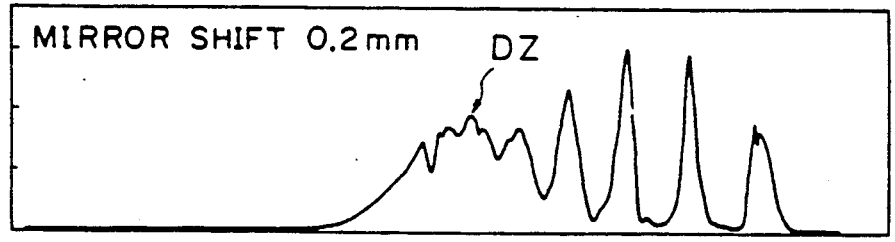
Figure 16C:
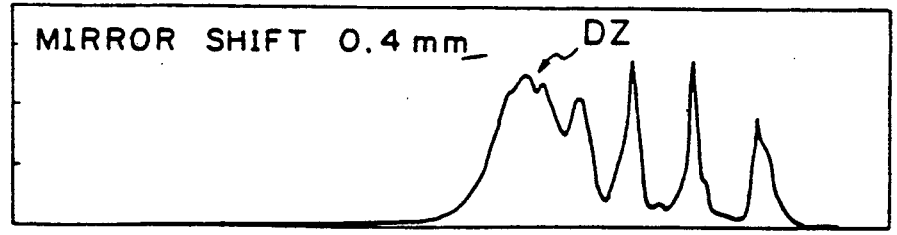
Figure 17A:
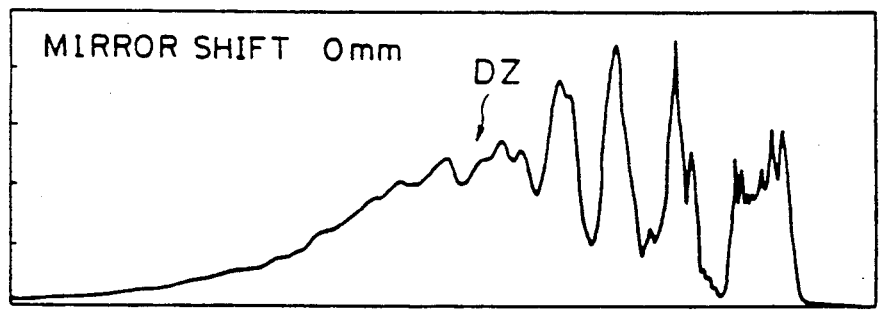
FIGS. 17A to 17C are graphs showing a characteristic representing a distribution of light intensity of a semiconductor laser beam curtain (coherence length of 1 mm) wherein the concave reflector was shifted within a predetermined range.
Figure 17B:
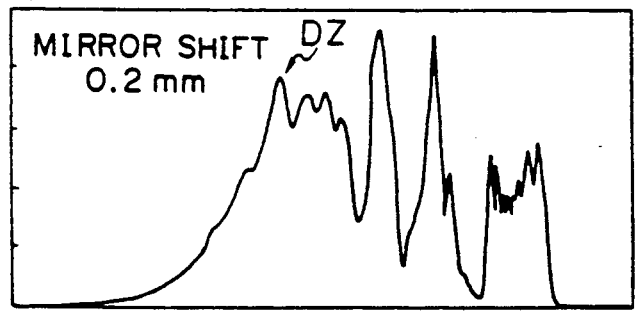
Figure 17C:
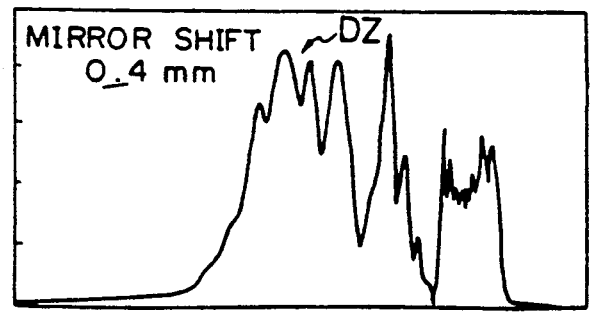

FIGS. 16A to 16C and FIGS. 17A to 17C show distributions of the light intensity of semiconductor laser beam curtains actually measured in the arrangement as shown in FIG. 13A, wherein a semiconductor laser beam was used instead of the He—Ne laser beam. In FIGS. 16A to 16C, a semiconductor laser beam (5 mW) having a common coherence length of more than 10 m was used, but in FIGS. 17A to 17C, a semiconductor laser beam (4.2 mW) having a coherence length of 1 mm was used. In FIGS. 16A to 16C, the distributions of light intensity were actually measured in three cases in which the concave $M_1$ remained at the initial position; was shifted by the distance of 0.2 mm; and by the distance of 0.4 mm, respectively. This also holds true for FIGS. 17A to 17C. As seen from FIGS. 16A to 16C and FIGS. 17A to 17C, in each detection zone indicated by DZ, the multi-reflected beam segments do not interfere with each other. Namely, the interference of the multi-reflected beam segments can be eliminated from the detection zone by using the semiconductor laser beam instead of the Ne-Ne laser beam, regardless of a coherence length of the semiconductor laser beam used.

Especially, as seen from FIGS. 21A to 21D, the distribution of light intensity of the semiconductor laser beam curtain may include a relatively narrow band having a uniform light intensity. Accordingly, if the relatively narrow band is used as a particle detection zone, not only can the presence of particles be detected, but also a size of the detected particle can be measured.

FIGS. 18A and 18B show waveforms of a detected pulse derived from the light scattered due to the presence of particles in the detection zone of the He—Ne laser beam (2 mW); FIGS. 19A and 19B show waveforms of a detected pulse derived from the light scattered due to the presence of particles in the detection zone of the semiconductor laser beam (8 mW) having the common coherence length of more than 10 m; and FIGS. 20A and 20B show waveforms of a detected pulse derived from the light scattered due to the presence of particles in the detection zone of the semiconductor laser beam (3.9 mW) having the coherence length of 1 mm. In FIGS. 18A and 18B, FIGS. 19A and 19B, and FIGS. 20A and 20B, the detected pulses are indicated by DP. Note, in FIGS. 18A and 18B, FIGS. 19A and 19B, and FIGS. 20A and 20B, latex particles having a size of 2 $\mu$m were used as the sample particles.

As seen from FIGS. 18A and 18B, when the He—Ne laser beam was sued, the detected pulse has a complicated waveform due to the interference of the multi-reflected beam segments. On the other hand, as seen from FIGS. 19A and 19B, and FIGS. 20A and 20B, when the semiconductor laser beam was used, the detected pulse had a simple waveform.

Figure 21A:
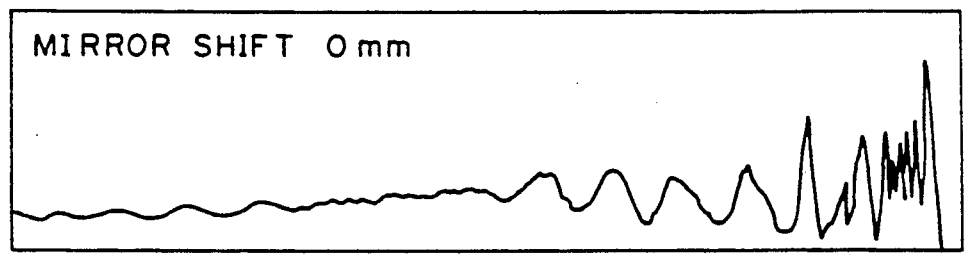
FIGS. 21A to 21E are graphs showing a characteristic representing a distribution of light intensity of a semiconductor laser beam curtain (wavelength of 780 nm) wherein the concave reflector was shifted within a predetermined range, the concave and convex reflector having the same radii of curvature.
Figure 21B:
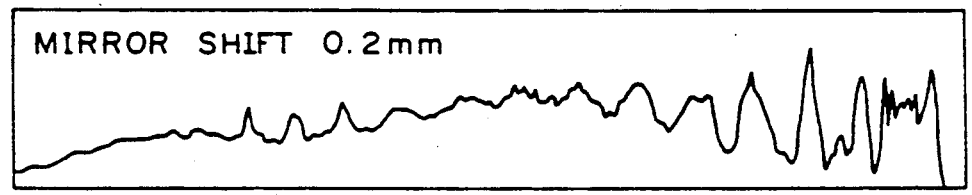
Figure 21C:
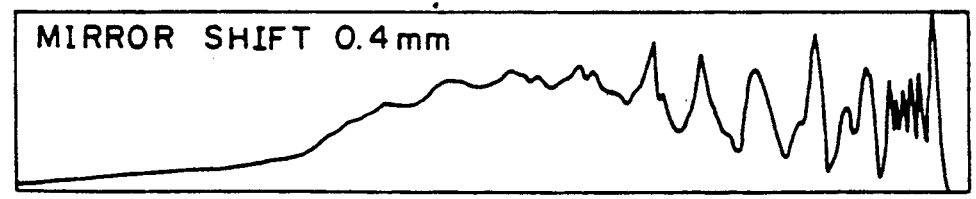
Figure 21D:
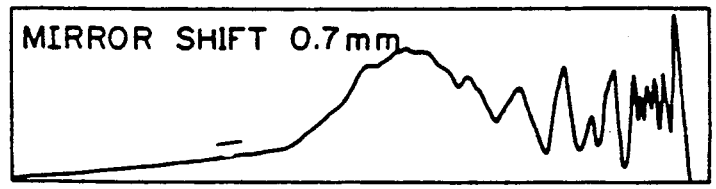
Figure 21E:
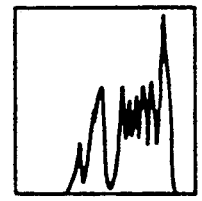

FIGS. 21A to 21D show distribution of light intensity actually measured in the arrangement of FIG. 13A, wherein a convex reflector having a radius of 1000 mm was used instead of the convex reflector $M_2$ having the radius of 900 mm; and wherein the semiconductor laser beam (wave length of 780 mm) having the common coherence length was used instead of the He—Ne laser beam. In FIGS. 21A to 21D, the distributions of light intensity were actually measured in four cases, in which the concave $M_1$ remained at the initial position; was shifted by the distance of 0.2 mm; by the distance of 0.4 mm, and by 0.7 mm, respectively. Note that FIG. 21E shows a light intensity of the introduced laser beam prior to reflection between the concave and convex reflectors, and this light intensity may be common in the characteristics shown FIGS. 21A to 21D.

As seen from FIGS. 21A to 21D, when the convex reflector having the radius of 1000 mm, and having a band which can be used as a detection zone, is wider than that shown in FIGS. 16A to 16C and FIGS. 17A to 17C, in which the convex reflector $M_2$ having the radius of 900 mm were used. This tendency was also found when convex reflectors having a radius of more than 1000 mm (1100 to 1200 mm) were used.

Figure 22A:
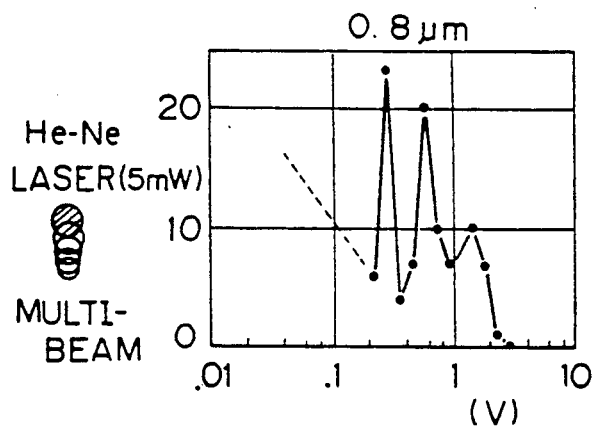
FIGS. 22A and 22B are graphs showing a distribution of voltages of detected pulses derived from sample particles of the same size, the sample particles being detected in the He—Ne laser beam curtain according to the present invention.
Figure 22B:
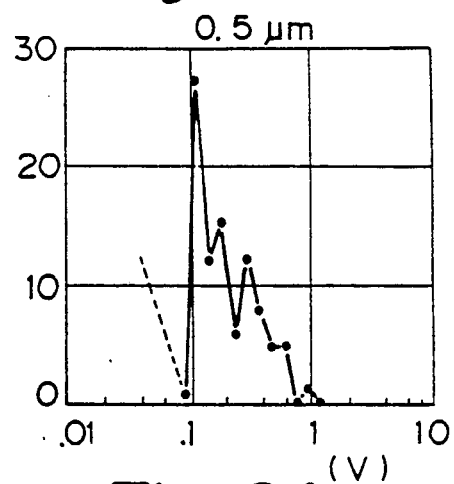

Furthermore, to determined a sensitivity of the particle detection according to the present invention, a detection of sample particles having a predetermined size was repeatedly performed. The results are shown in FIG. 22A and 22B, in which the abscissa shows a voltage of the detected pulses and the ordinate shows a number of the detected pulses. Namely, FIGS. 22A and 22B shows a distribution of voltages of the detected pulses derived from sample particles having the same size.

Figure 23:
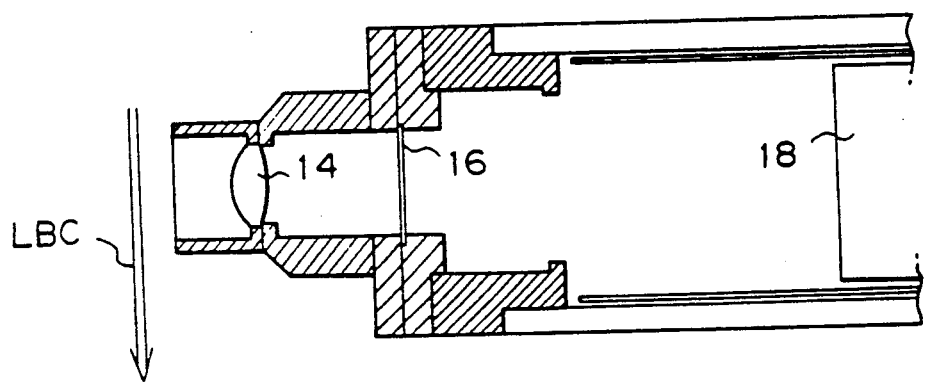
FIG. 23 is a longitudinal sectional view showing a light detector for measuring the distribution of FIGS. 22A and 22B.

In FIGS. 22A and 22B, the He—Ne laser beam (5 mW) was used and was multi-reflected according to the present invention (in the arrangement as shown in FIG. 13A). A light detector as shown in FIG. 23 was used for detecting the scattered light. The light detector comprises a lens 14 (f 8.5 mm; o12 mm) for receiving the light scattered from the laser beam curtain LBC due to the presence of particles, a slit member 16 for defining an area to be detected on the laser beam curtain LBC, and a photomultiplier tube 18 for converting the light filtered by the slit member 16 into an electric signal. In FIG. 22A, particles having a size of 0.8 $\mu$m were used as sample particles, whereas in FIG. 22B, particles having a size of 0.5 $\mu$m were used as the sample particles.

Figure 24A:
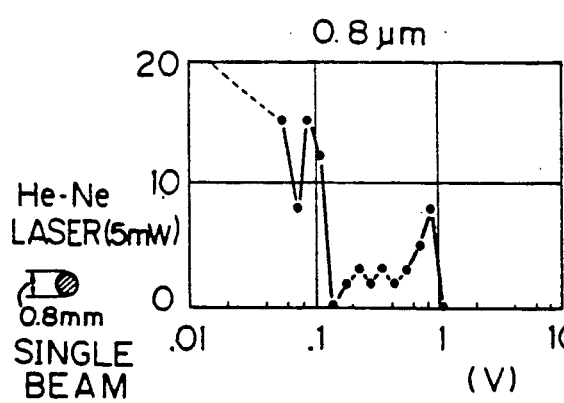
FIGS. 24A and 24B are graphs showing a distribution of voltages of detected pulses derived from sample particles of the same size, the sample particles being detected in the single He-Ne laser beam.
Figure 24B:
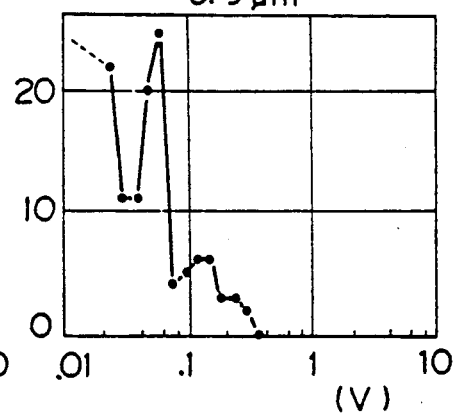

FIGS. 24A and 24B show distributions of voltages of the detected pulses derived from sample particles having the same size, wherein a single He—Ne laser beam (5 mW) having a diameter of 0.8 mm, as shown in FIG. 24A, was used instead of the laser beam curtain according to the present invention. In FIG. 24A, particles having a size of 0.8 $\mu$m were used as sample particles, whereas in FIG. 24B, particles having a size of 0.5 $\mu$m were used as the sample particles.

Figure 25:
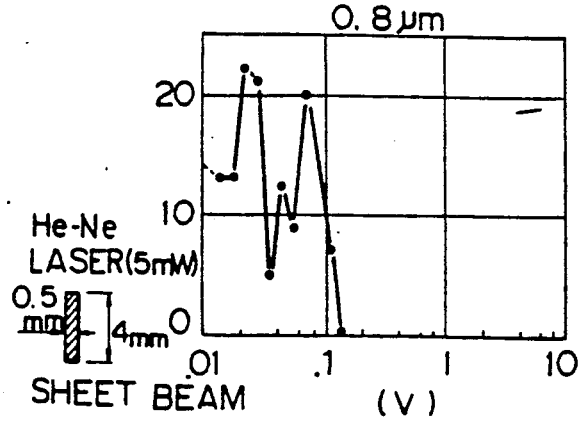
FIG. 25 is a graph showing a distribution of voltages of detected pulses derived from sample particles of the same size, the sample particles being detected in the sheet-like He-Ne laser beam.

FIG. 25 shows a distribution of voltages of the detected pulses derived from the sample particles having a size of 0.8 $\mu$m, wherein a sheet-like He—Ne laser beam was used instead of the laser beam curtain according to the present invention. To obtain the sheet-like laser beam, the He—Ne laser beam (5 mW) was deformed by a cylindrical lens so that the deformed beam had a width of 4.0 mm and a thickness of 0.5 mm at half maximum, as shown in FIG. 25.

As seen from the comparison of FIGS. 22A and 22B with FIGS. 24A and 24B and FIG. 25, the sensitivity of particle detection according to the present invention was a considerable improvement over the conventional detection.

Figure 26:
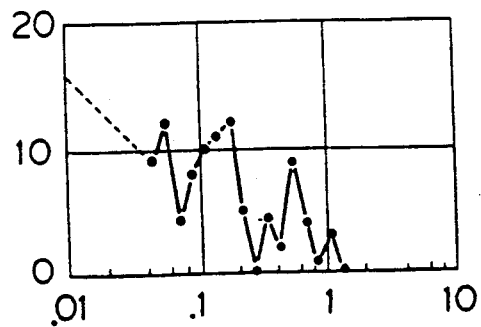
FIG. 26 is a graph showing a distribution of voltages of detected pulses derived from sample particles of the same size, the sample particles being detected in the semiconductor laser beam curtain according to the present invention.
Figure 27:
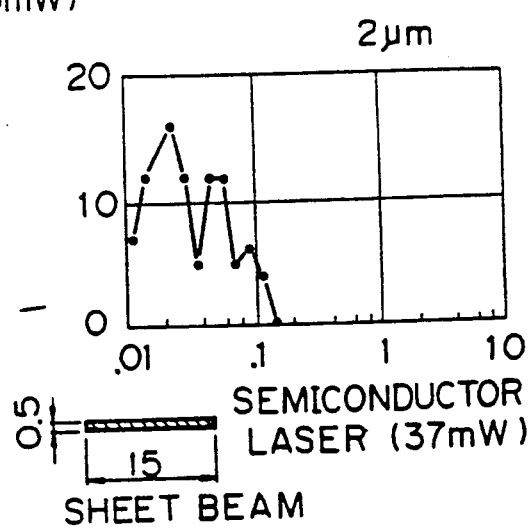
FIG. 27 is a graph showing a distribution of voltages of detected pulses derived from sample particles of the same size, the sample particles being detected in the sheet-like semiconductor laser beam.

FIG. 26 shows a distribution of voltages of the detected pulses derived from sample particles having a size of 2 $\mu$m, wherein a semiconductor laser beam (5.5 mW) was used instead of the He—Ne laser beam and was multi-reflected according to the present invention (in the arrangement as shown in FIG. 13A). FIG. 27 shows a distribution of voltages of the detected pulses derived from sample particles having a size of 2 $\mu$m, wherein a semiconductor laser beam (37 mW) was used but was deformed into a sheet-like laser beam by a cylindrical lens so that the deformed beam had a width of 4.0 mm and a thickness of 0.5 mm at half maximum, as shown in FIG. 27. As seen from the comparison of FIG. 26 with FIG. 27, when the semiconductor laser beam was used, the sensitivity of particle detection according to the present invention was again an improvement.

According to the embodiments of the present invention described above, it is possible to detect the presence of particles with a high probability and a high sensitivity by multi-reflecting the laser beam at a much closer pitch in the detection zone, but it is impossible to determine a size of the detected particle because the particle detection zone do not have a uniform distribution of light intensity, as shown in FIG. 14, FIGS. 16A to 16C, FIGS. 17A to 17B, and FIG. 21A to 21D. This can be also understood from FIGS. 22A and 22B and FIG. 26.

Figure 28:
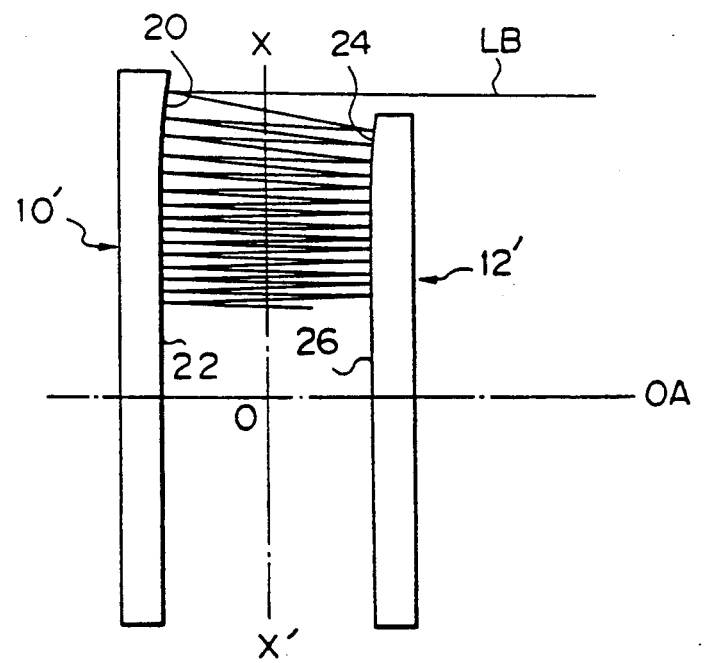
FIG. 28 is a view showing an arrangement of partial concave and convex reflectors in which a laser beam curtain has a substantially uniform light intensity distribution.

Namely, in these embodiments, the laser beam can be multi-reflected at a much closer and uniform pitch in the detection zone, but by using two reflectors which have partially concave and convex reflecting surfaces, respectively, as shown in FIG. 28, it is possible to multi-reflect the laser beam at a much closer and uniform pitch, whereby not only can the presence of particles be detected with a high probability and a high sensitivity, but also a size and a number of the detected particles can be determined.

In FIG. 28, the partial concave reflector 10, has a concave reflecting zone 20 and a plane reflecting zone 22 smoothly continuing from the concave zone 20, and the partial convex reflector 12' has a convex reflecting zone 24 and a plane reflecting zone 26 smoothly continuing from the convex zone 24. In the arrangement of the reflectors 10' and 12' as shown in FIG. 28, the laser beam LB, which is introduced therebetween in parallel with optical axis OA, is multi-reflected between the concave and convex zones 20 and 24 in such a manner that a pitch of the reflection becomes gradually closer, and is then multi-reflected between the plane zones 22 and 26 in such a manner that the much closer pitch obtained by the reflection between the concave and convex zones 20 and 24 is maintained, whereby the laser beam curtain formed between the plane zones 22 and 26 can have a substantially uniform distribution of light intensity along an axis X-X' which is perpendicular to the optical axis OA and which extends along the center line of the laser beam curtain between the plane zones 22 and 26. In the laser beam curtain having the substantially uniform distribution of light intensity, it possible to measure an unknown size and an unknown number of detected particles by previously determining a sample particle having a known size, because a strength of the light scattered due to the presence of particles in the substantially uniform distribution of light intensity depends on a size of the detected particles.

Figure 29:
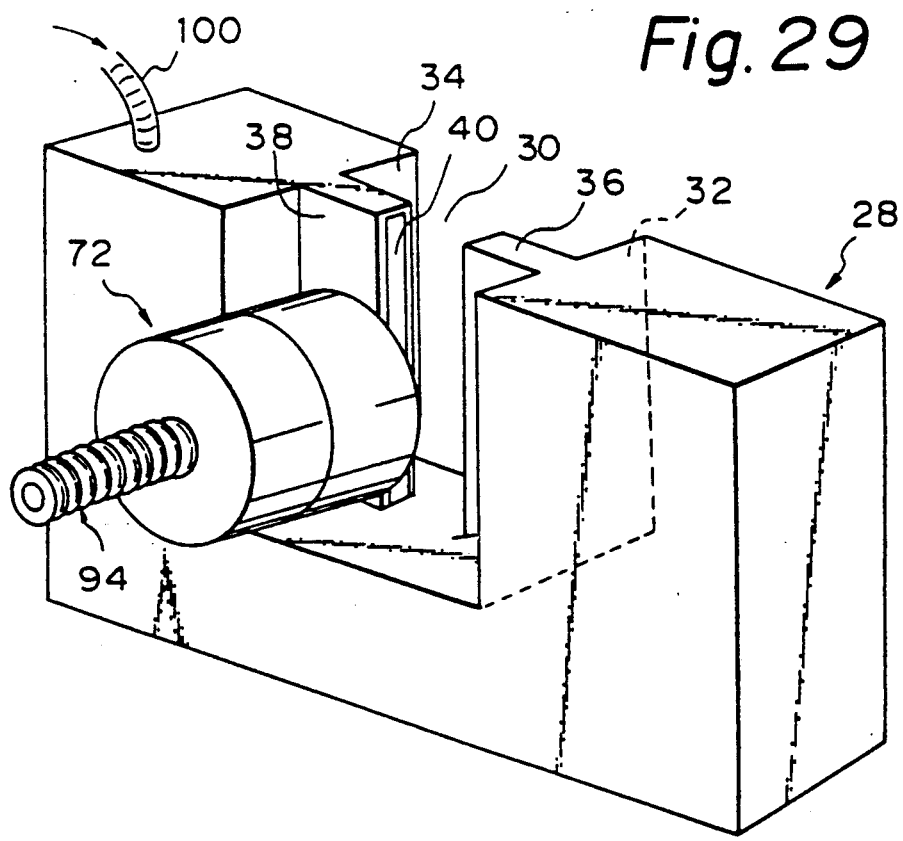
FIG. 29 is a perspective view showing a particle detection apparatus according to the present invention.

FIG. 29 shows a particle detection apparatus to which the principle of the present invention is applied, and which is constructed to be used in a vacuum chamber (not shown) for the formation of a thin film element by, for example, a sputtering process. The particle detection apparatus comprises a housing 28 having substantially a U-shape. The housing 28 has a rectangular central recess 30 resulting from the U-shape thereof, the recess 30 being defined the opposed inner side faces 32 and 34. The inner side faces 32 and 34 are provided with rectangular hollow members 36 and 38 protruding therefrom, respectively. The hollow members 36 and 38 have opposed rectangular elongated openings, only one of the rectangular elongated openings being indicated by reference numeral 40 in FIG. 30. A laser beam curtain according to the present invention is formed between the rectangular hollow members 36 and 38, as mentioned hereinafter.

Figure 30:
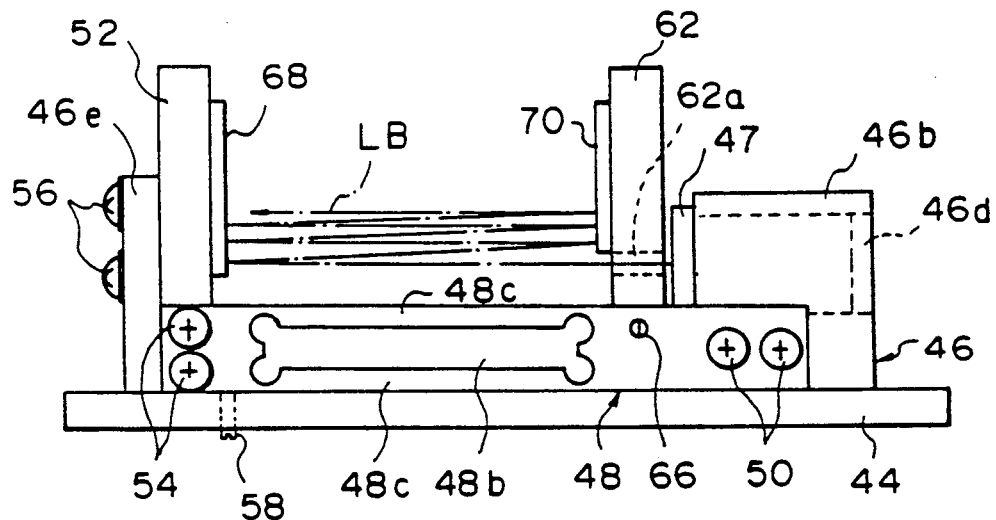
FIG. 30 is a front view showing an optical assembly of the present invention.
Figure 32A:
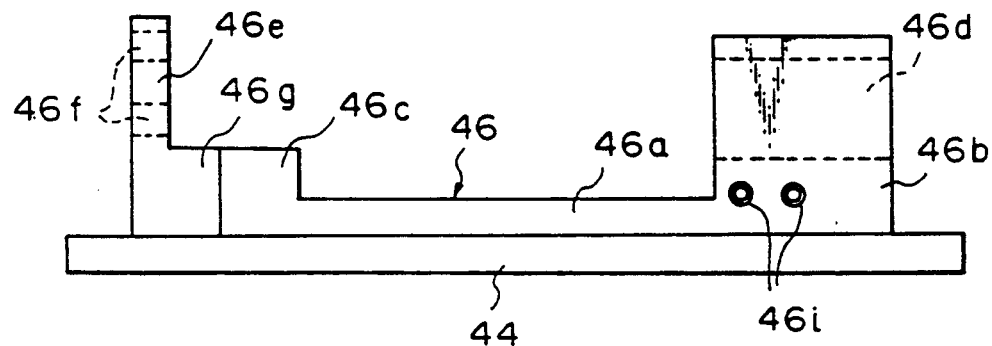
FIG. 32A is a front view showing a base plate and a mount base of the optical assembly shown in FIG. 30.
Figure 32B:
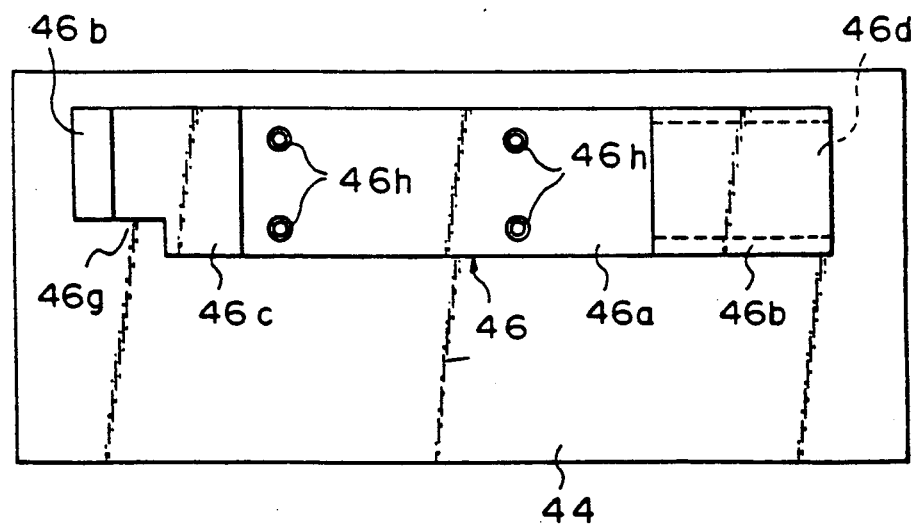
FIG. 32B is a plane view of FIG. 32A.

An optical assembly, generally indicated by reference numeral 42 in FIGS. 30 and 32, is housed within the housing 28. The optical assembly 42 includes a rectangular base plate 44 on which a mount base 46 is fixedly secured. As best shown in FIGS. 32A and 32B, the mount base 46 includes a base portion 46a, a first raised portion 46b integrally formed on one end of the base portion 46a, and a second raised portion 46c integrally formed on the other end of the base portion 46a. The first raised portion 46b has a bore 46d formed therethrough, and a laser source or a laser generator 47 is mounted in the bore 46b of the first raised portion 46b. The laser generator 47 includes a semiconductor laser device which may emit a laser beam having a wave length of, for example, 780 nm. The second raised portion 46c includes an upright member 46e which vertically and upwardly extends therefrom, and which has a pair of oval holes 46f formed therethrough. The second raised portion 46c also has a recess 46g formed at a corner thereof, and the base portion 46a has four threaded holes 46h formed therein as shown in FIG. 32B.

Figure 33A:
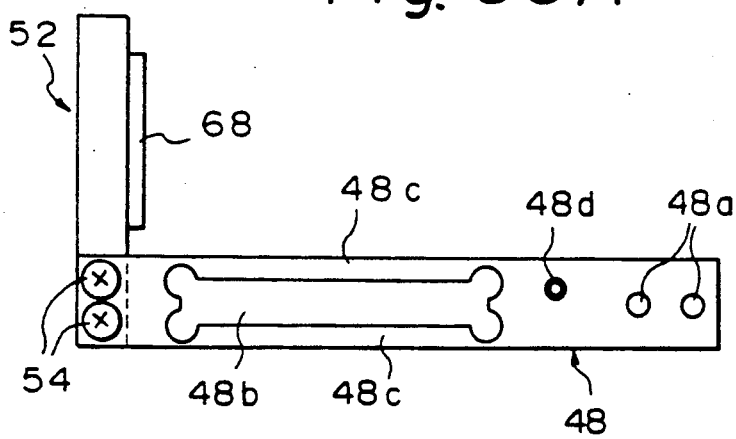
FIG. 33A is a front view showing a first plate-like arm member and a first vertical plate member attached thereto of the optical assembly shown in FIG. 30.
Figure 33C:
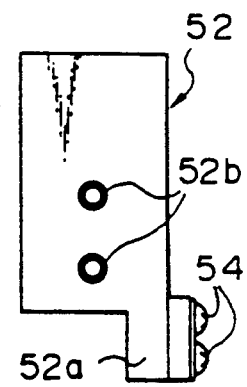
FIG. 33C is a side view of FIG. 33A.
Figure 33B:
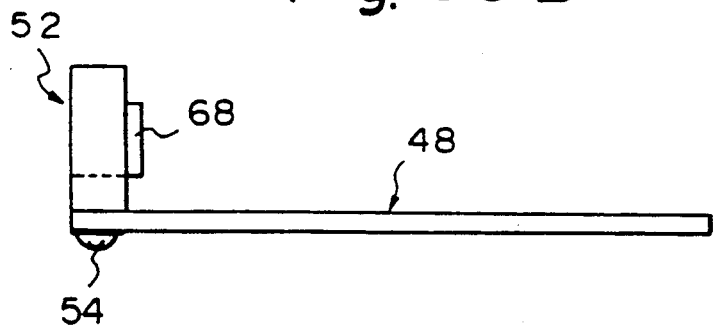
FIG. 33B is a plane view of FIG. 33A.

The optical assembly 42 also includes a first plate-like arm member 48 which is fixedly attached at one end thereof to a side face of the first raised portion 46b by a pair of screws 50 and 50 so as to extend along the upper surface of the base plate 44. As best shown in FIGS. 33A to 33C, the first plate-like arm member 48 has a pair of holes 48a formed at one end thereof for inserting the screws 50 which are screwed into threaded holes 46i (FIG. 32A) formed in the side face of the first raised portion 46b. A first vertical plate member 52 is secured to the other end of the first plate-like arm member 48 by a pair of screws 54 and 54. In particular, the first vertical plate member 52 has a portion 52a extending from a corner thereof, as shown in FIG. 33C, the other end of the first plate-like arm member 48 being secured to an outer side of the extended portion 52a of the first vertical plate member 52. The first vertical plate member 52 also has a pair of threaded holes 52b formed therethrough as shown in FIG. 33C. As seen from FIGS. 30 and 33A, an elongated opening 48b is formed in the first plate-like arm member 48 so that the opposed thin portions 48c remain therein.

When the first vertical member 52 is attached to the first raised portion 46b as mentioned above, the extended portion 52a of the first vertical plate member 52 is received in the recess 46g of the second raised portion 46c so that the first vertical plate member 52 is aligned with the upright member 46e of the second raised portion 46c. The first vertical plate member 52 is connected to the upright member 46e by a pair of screws 56 which are inserted through the oval holes 46f and screwed into the threaded holes 52b, but the first vertical plate member 52 is can be shifted in the vertical direction because the holes 46f have the oval-shaped cross section and because the opposed thin portions 48c of the first plate-like arm member 48 can be deformed.

As shown in FIG. 30, a set screw 58 is screwed into the base plate 44 and abutted against the end portion of the first plate-like arm member 48, which is attached to the first vertical plate member 52. Accordingly, the first vertical plate member 52 is adjustable in the vertical direction by screwing the set screw 58.

Figure 31:
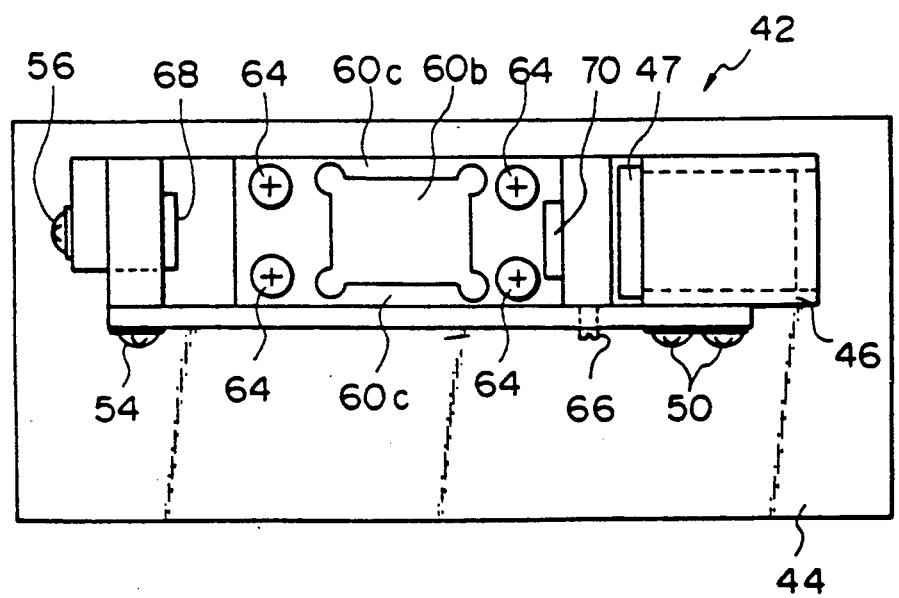
FIG. 31 is a plane view of FIG. 30.
Figure 34A:
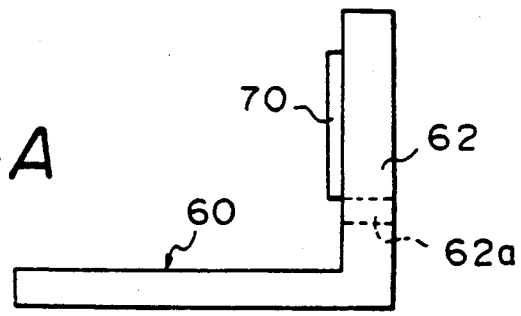
FIG. 34A is a front view showing a second plate-like arm member and a second vertical plate member integrally formed therewith of the optical assembly shown in FIG. 30.
Figure 34B:
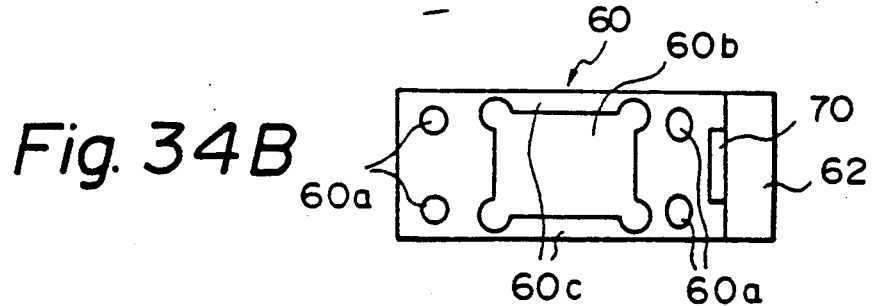
FIG. 34B is a plane view of FIG. 34A.

The optical assembly 42 also includes a second plate-like arm member 60 which is disposed on the base portion 46a of the mount base 46. As best shown in FIGS. 34A and 34B, the second plate-like arm member 60 includes a second vertical plate member 62 which is integrally formed at one end thereof to extend vertically and upwardly. As apparent from FIG. 34B, the second plate-like member 60 has four holes 60a which are formed therethrough so that they are arranged in the vicinity of the four corners of the second plate-like member 60, respectively. The arrangement of the four holes 60a corresponds to that of the four holes 46h formed in the base portion 46a of the mount base 46 so that, when the second plate-like arm member is disposed on the base portion 46a, each of the holes 60a is aligned with the corresponding hole 46h. Note that two of the holes 60a which are disposed beside the second vertical plate member 62 have an oval-shaped cross section as shown in FIG. 34B. A rectangular opening 60b is formed in the second plate-like arm member 60 so that the opposed thin portions 60c remain therein. The second plate-like arm member 60 is fixedly mounted on the base portion 46a of the base mount 46 by four screws 64 (FIG. 31) which are inserted through the four holes 60a and screwed into the threaded holes 46h, respectively, but the second vertical plate member 62 is can be shifted in the horizontal direction because said two of the holes 60a have the oval-shaped cross section and because the opposed thin portions 60c of the second plate-like arm member 60 can be deformed. As shown in FIGS. 30 and 31, a set screw 66 is screwed into a threaded hole 48d (FIG. 33A) of the first plate-like arm member 48 and abutted against the second vertical plate member 62. Accordingly, the second vertical plate member 62 is adjustable in the horizontal direction by screwing the set screw 66.

As apparent from the foregoing, by suitably adjusting the set screws 58 and 66, the first and second vertical plate members 52 and 62 can be shifted relative to each other in the horizontal and vertical directions or X and Y directions perpendicular to each other.

The first and second vertical plate members 52 and 62 are provided with concave and convex reflectors 68 and 70 fixedly attached to the opposed surfaces thereof, respectively. In this embodiment, the concave reflector 68 has a radius of curvature of 1000 mm, and the convex reflector 70 has a radius of curvature thereof being 900 mm. A distance between the concave and convex reflectors 68 and 70 is set at 50 mm when measured along the optical axis. The second vertical plate member 62 has a bore 62a (FIGS. 30 and 34A) formed therein, through which the laser beam LB emitted from the laser generator 47 passes and is incident on the concave reflector 68. Since the first and second vertical plate members 52 and 62 can be shifted relative to each other in the X and Y directions, the relative position between the concave and convex reflectors 68 and 70 is adjustable as explained with reference to FIGS. 3A and 3B and FIGS. 4A to 4C, whereby the concave and convex reflectors 68 and 70 can be arranged so that the laser beam LB is multi-reflected therebetween in accordance with the present invention.

The optical assembly 42 is housed within the housing 28 so that the concave and convex reflectors 68 and 70 are opposed to the elongated openings (40) of the rectangular hollow members 38 and 36, respectively, whereby the laser beam curtain can be formed between the elongated openings (40).

Figure 35A:
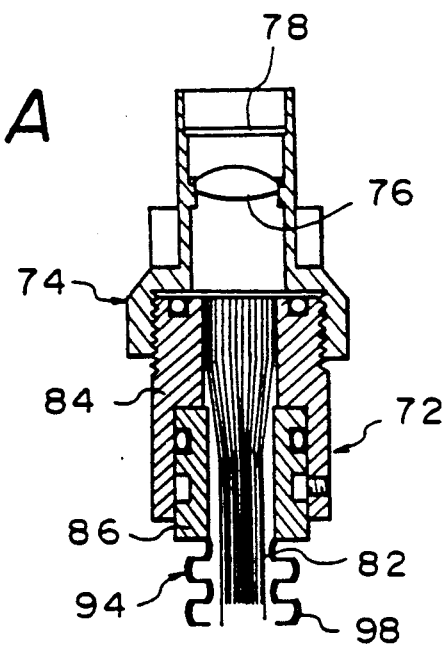
FIG. 35A is a longitudinal sectional view of a detector head forming a part of a light detector device.
Figure 35B:
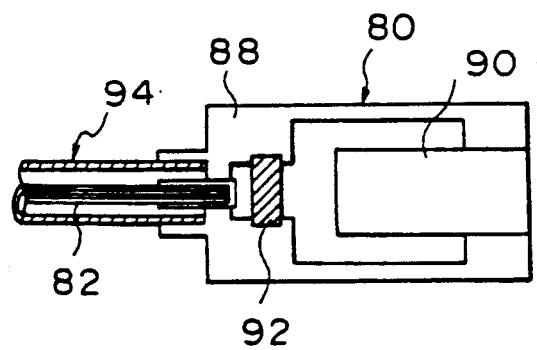
FIG. 35B is a longitudinal sectional view of a detector body forming a part of the light detector device.

The particle detection apparatus also comprises a light detector device 72 (FIG. 29) for receiving light scattered due to the presence of particles in the laser beam curtain. The light detector device 72 includes a detector head or hollow tubular member 74, as shown in FIG. 35A, which is supported in place by, for example, the housing 28, so that a front opening of the detector head 74 faces the laser beam curtain. The detector head 74 is provided with a lens 76 for receiving the scattered light and a transparent plate 78 for protecting the lens 76 from polluting by particles generated during the sputtering process. The detector head 74 is connected to a detector body 80 (FIG. 35B) through a bundle of optical fibers 82. The detector body 80 forms a part of the detector device 72, but it is disposed outside the vacuum chamber of the sputtering equipment. One end of the optical fiber bundle 82 is coupled to the detector head 74 by coupling members 84 and 86, and the end face thereof serves as a light receiving face for the scattered light. The other end of the optical fiber bundle 89 is connected to a casing 88 of the detector body 80, and the end face thereof faces a light receiving face of a photomultiplier tube 90 housed in the casing 88 through the intermediary of an optical filter 92. Accordingly, the scattered light received by the lens 76 is transmitted to the detector body 80 through the optical fiber bundle 82, and is then received by the photomultiplier tube 90 to be converted into an electrical signal. Although light generated during the sputtering process is received as a noise together with the scattered light by the lens 76 and is then transmitted to the detector body 80 through the optical fiber bundle 82, it can be eliminated by the optical filter 92. The optical fiber bundle 82 is covered by a metal tube 94 which extends from the detector head 74 to the detector body 80 so that air cannot enter the vacuum chamber of the sputtering equipment through the passage for transmitting the scattered light. Note that the metal tube 94 is sealingly passed through a wall 96 (FIG. 35C) defining the vacuum chamber of the sputtering equipment. As partially shown in FIGS. 35A and 35C, at least a portion of the metal tube 94 is preferably formed as a bellows 98, so that it can be easily bent.

Preferably, an inert gas such as argon is introduced into the housing 28 through a pipe 100 (FIG. 29) which is connected to a suitable inert gas source (not shown), so that the inert gas is discharged from the elongated openings (40) of the rectangular hollow members 36 and 38, whereby pollution of the concave and convex reflectors 68 and 70 by the particles which are generated during the sputtering process is prevented.

In this embodiment, the scattered light is transmitted to the photomultiplier tube 90 through the intermediary of the optical fiber bundle 82, as mentioned above, because the optical assembly 24 with the housing 28 must be disposed within the vacuum chamber of the sputtering equipment. However, when the particle detection apparatus is applied to, for example, a clean room for the production of semi-conductors, the photomultiplier tube may be directly incorporated into the detector head.

Figure 36A:
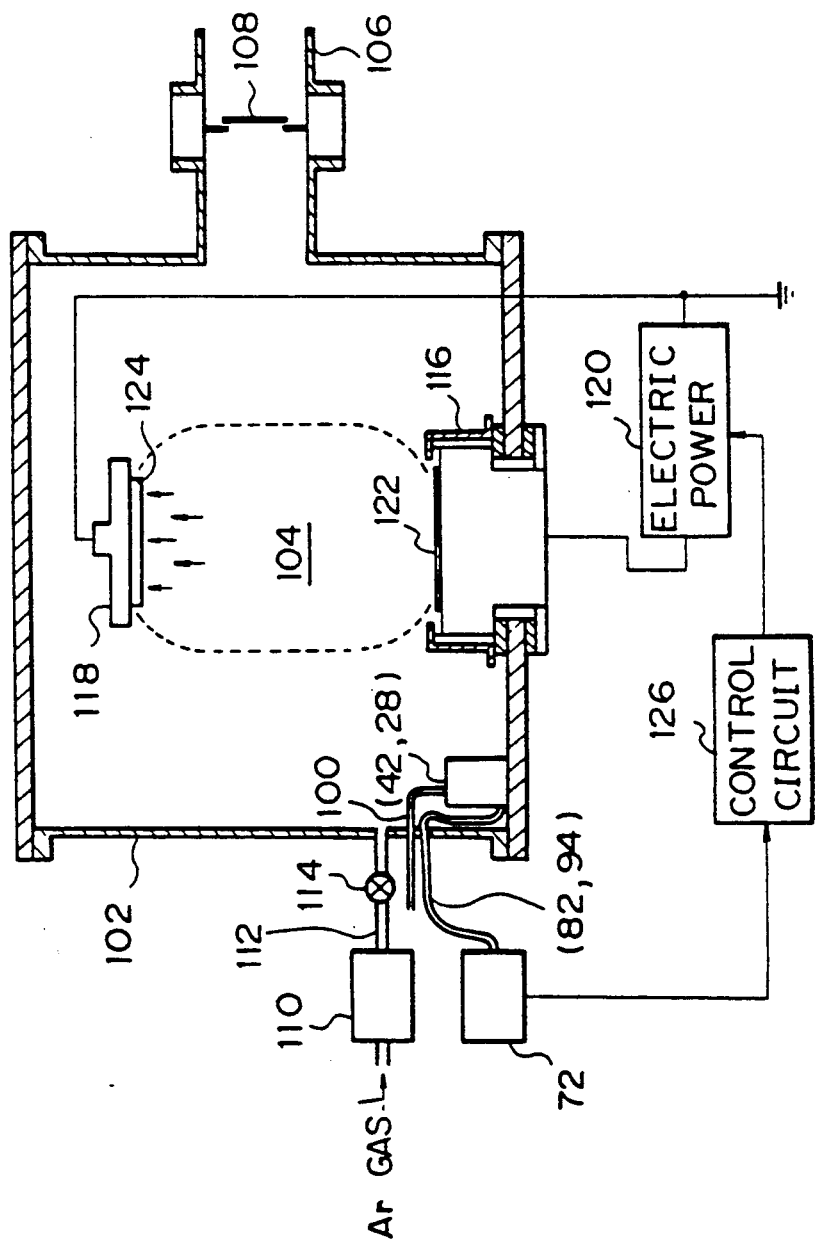
FIG. 36A is a schematic cross sectional view showing a sputtering equipment into which the optoelectrical particle detection apparatus is incorporated.

FIG. 36A shows a sputtering equipment into which the optoelectrical particle detection apparatus as mentioned above is actually incorporated. The sputtering equipment includes a vessel 102 defining a vacuum chamber 104. The vessel 102 is provided with a discharge duct 106 adapted to be connected to a vacuum pump (not shown) such as a diffusion pump, whereby air can be drawn from the vacuum chamber 104 through the discharge duct 106. The discharge duct 106 has a valve 108 provided therewithin, which is regulated to maintain a pressure in the vacuum chamber 104 at a predetermined degree of vacuum. The sputtering equipment also includes an argon gas source 110 is communicated with the vacuum chamber 104 through a pipe 112 provided with a valve 114. As is well known, during the sputtering process, the vacuum chamber 104 is filled with argon gas. Note that the argon gas source 110 may be utilized to feed argon gas into the housing 28 of the optical assembly 42 (FIG. 29).

The sputtering equipment further includes a target assembly 116 sealingly installed in a bottom of the vessel 102, a substrate assembly 118 facing the target assembly 116 within the vacuum chamber 104, and an electric source 120 for applying a voltage between the target assembly 116 and the substrate assembly 118. The substrate assembly 118 may be suitably supported from a top wall of the vessel 102. The electric source 120 may comprise a radio frequency electric source or a direct-current electric source. Alternatively, both the radio frequency electric source and the direct-current electric source may be provided, and one of these sources selected by a two-way switch (not shown). A target 122 is applied to the target assembly 116, while a substrate 124 is held by the substrate assembly 118.

As well known, in the sputtering process, argon ions ($Ar^+$) are generated in space between the target 122 and the substrate 124, and are then incident on the target 122, whereby atoms of the target material are emitted from the target 122 toward the substrate 124 as shown by arrows in FIG. 36A, so that the atoms are deposited on the substrate 124 to form a thin film thereon. As long as only the atoms of the target material are emitted, the formation of a thin film is properly carried out, but, for example, when an abnormal glow discharge occurs, aggregations of the atoms are emitted as dust particles from the target, and thus defects may occur in the formed thin film.

Figure 35C:
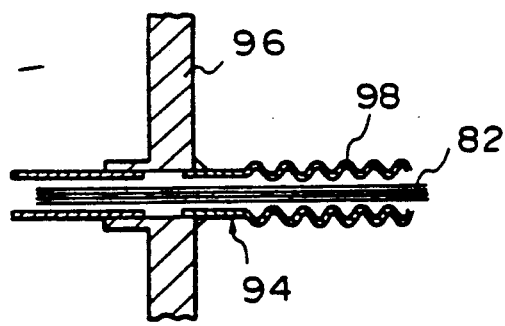
FIG. 35C is a longitudinal sectional view showing a portion of a metal tube for covering a bundle of optical fibers to connect the detector head and the detector body, the metal tube being sealingly passed through a wall defining a vacuum chamber.

The optoelectrical particle detection apparatus according to the present invention is incorporated into the sputtering equipment to control same. As shown in FIG. 36A, the optical assembly 42 housed in the housing 28 is installed on the bottom of the vessel 102 apart from the target assembly 116, and the light detector device 72 is disposed outside the vessel 102. Although not shown in FIG. 36A, the detector head 74, which forms a part of the light detector device 72, is supported by the housing 28 and connected to the detector body 80, which also forms a part of the light detector device 72, through the optical fiber bundle 82 covered by the metal tube 94, which is sealingly passed through the wall of the vessel 102 as shown in FIG. 35C. To control the sputtering equipment, an output side of the light detector device 72 is connected to an input side of a control circuit 126, an output side of which is then connected to the electrical source 120 to regulate a power output by the electrical source 120. The control circuit 126 includes an analog/digital converter (A/D converter) for converting an analog signal (output from the photomultiplier tube 90 of the detector body 80) into a digital signal. In particular, the A/D converter includes a low pass filter circuit or an integrating circuit. That is, in the A/D converter, an output signal from the photomultiplier tube 90 is integrated and converted into a digital signal. Thus, the converted digital signal represents the number of dust particles captured by the laser beam curtain per unit time.

The control of the sputtering equipment will be now explained with reference to a routine shown in FIG. 36B. This routine is initiated by turning ON a power supply to the control circuit 126.

When the dust particles emitted from the target are captured by the laser beam curtain formed in the optical assembly 42 as mentioned above, light scattered from the captured dust particles is received by the detector head 74 and then transmitted to the photomultiplier tube 90 of the detector body 80 through the optical fiber bundle 82, and thus the photomultiplier tube 90 outputs a voltage which varies in accordance with the number of the captured dust particles and the size thereof.

In step 361 of the routine, the digital signal converted by the A/D converter is fetched as digital data VL. Then, in step 362, it is determined whether or not the digital data VL is larger than a threshold $V_0$, which is stored in a memory of the control circuit 126. If the digital data VL is larger than the threshold $V_0$, namely, if the presence of dust particles is detected in the laser beam curtain, the control proceeds to step 363 in which the power from the electrical source 120 is abruptly lowered by 10%, to suppress the emission of the dust particles.

In step 364, it is determined whether or not a time of 0.5 sec. is passed. When the time of 0.5 sec. is passed, the control is returned to step 361. In other words, digital data VL is again fetched from the A/D converter, and then it is determined whether or not the digital data VL is larger than the threshold $V_0$. If $VL>V_0$, the power from the electrical source 120 is further lowered by 10%. In short, as long as $VL>V_0$, the power is lowered.

On the other hand, in step 362, if $VL<V_0$, namely, if the presence of dust particles is not detected in the laser beam curtain, the control proceeds to step 365 in which it is determined whether or not the power from the electrical source 120 is 100%. If the power is lower than 100%, the control proceeds to step 366 in which the power is raised by 1%. Then, in step 364, it is determined whether or not a time of 0.5 sec. is passed. When the time of 0.5 sec. is passed, the control is returned to step 361. That is, digital data VL is fetched from the A/D converter, and then it is determined whether or not the digital data VL is larger than the threshold $V_0$. If $VL<V_0$, the power from the electrical source 120 is further raised by 1%. In step 365, if the power is 100%, the control is returned from step 365 to step 361. In short, although the power from the electrical source 120 is once lowered due to the detection of the dust particles, the power is recovered to a normal level (100%). Note, the threshold $V_0$ can be obtained by experimental.

Figure 36C:
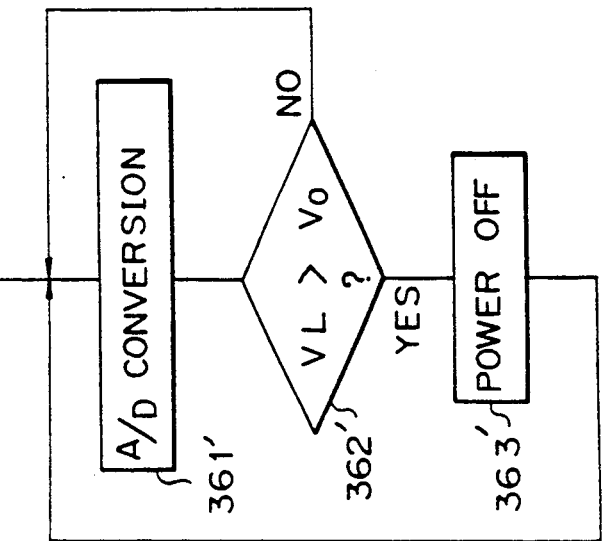
FIGS. 36B and 36C are sputtering control routines for explaining an operation of the sputtering equipment of FIG. 36A.
Figure 36B:
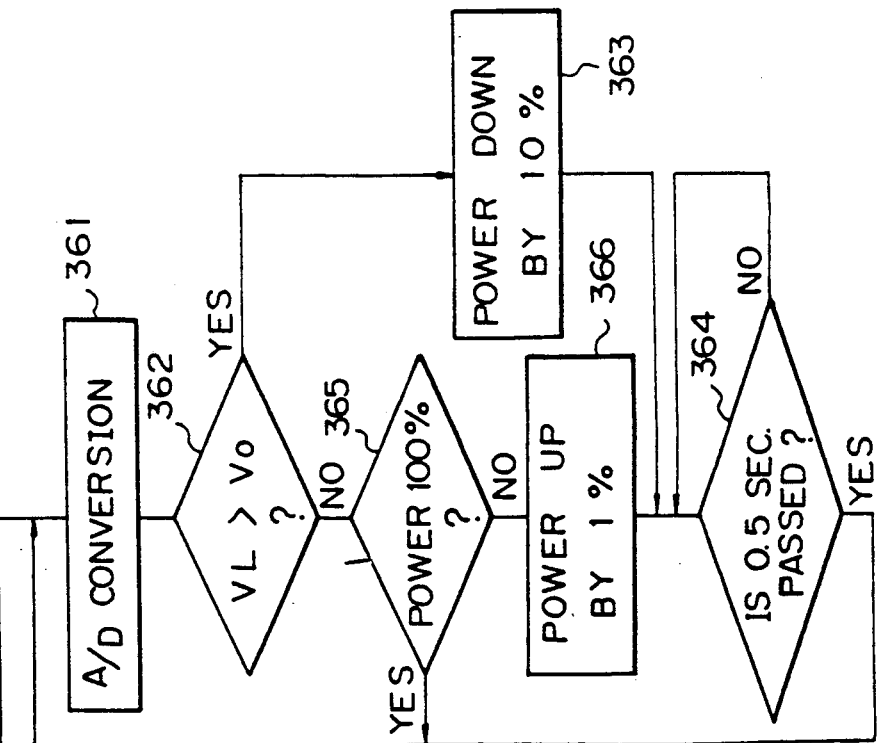

FIG. 36C shows another sputtering control routine which is initiated by turning ON a power supply to the control circuit 126.

In step 361', the digital signal converted by the A/D converter is fetched as digital data VL. Then, in step 362', it is determined whether or not the digital data VL is larger than the threshold $V_0$. If the digital data VL is larger than the threshold $V_0$, the control proceeds to step 363' in which the power from the electrical source 120 is turned OFF. In step 362', if $VL<V_0$, the control is returned to step 361'. Namely, in this routine, the emission of the dust particles is avoided by turning OFF the power from the electric source 120, and the power is manually recovered thereafter.

As mentioned, by monitoring the emission of the dust particles, it is possible to carry out the formation of a thin film on the substrate 124 with a high quality. Preferably the digital data VL is recorded by a suitable recorder (now shown) controlled by the control circuit 126, because this data can be used to evaluate a quality of the formed thin film.

Figure 37:
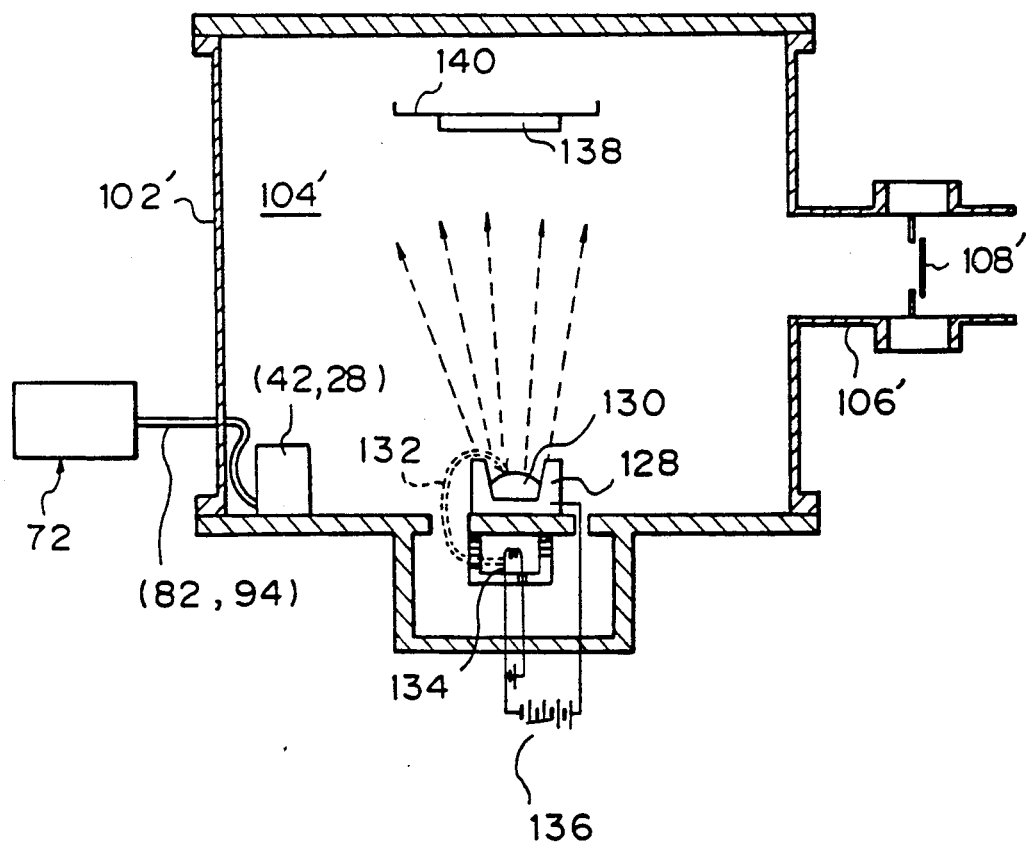
FIG. 37 is a schematic cross sectional view showing a vacuum evaporation equipment into which the optoelectrical particle detection apparatus is incorporated.

The particle detection apparatus according to the present invention can be also incorporated into another thin film formation equipment for, for example, carrying out a vacuum evaporation process as shown in FIG. 37. The vacuum evaporation equipment includes a vessel defining a vacuum chamber, which can be substantially constructed in the same manner as in FIG. 36A. Therefore, in FIG. 37, like elements of the vessel are given the same reference numerals with prime suffix.

As shown in FIG. 37, the vacuum evaporation equipment includes a hearth 128 installed on a bottom of the vessel 102' to receive an ingot 130. The ingot 130 is heated and melted in the hearth 128 by an electron beam 132 generated from a filament 134 energized by a direct-current electric source 136, and magnetically deflected to be incident on the ingot 130. The molten ingot 130 is evaporated as shown by arrows in FIG. 37, thereby causing atoms of the ingot material deposited on a substrate 138 held by a substrate holder 140 to form a thin film thereon. Similar to the sputtering equipment as shown in FIG. 36A, as long as only the atoms of the ingot material are evaporated, the formation of a thin film is properly carried out, but, for example, when an abnormal evaporation occurs, aggregations of the atoms may be generated and scattered as dust particles from the molten ingot 130, and thus defects may be caused in the formed thin film. To monitor the generation of the dust particles, the particle detection apparatus (42, 28, 72, 82, 94) according to the present invention is incorporated into the vacuum evaporation equipment as shown in FIG. 37. Note that, in the vacuum evaporation equipment, the housing 28 is not fed with argon gas. It is, of course, obvious that the vacuum evaporation equipment can be substantially controlled according to the generation of the dust particles, in the same manner as explained with reference to FIGS. 36A to 36C. In short, when a number of dust particles more than a predetermined level are detected, the generation thereof can be avoided by lowering the power from the electric source 136 or by turning it OFF.

Finally, it will be understood by those skilled in the art that the foregoing description is of preferred embodiments of the present invention, and that various changes and modifications can be made without departing from the spirit and scope thereof.

We claim:

1. An optoelectrical particle detection apparatus comprising:

concave and convex reflectors having spherical concave and convex reflecting surfaces, respectively, and spaced from each other by a predetermined distance to form a reflection space therebetween;

a laser source for emitting a laser beam and introducing the laser beam from a side of said reflection space thereinto to be multi-reflected to form a laser beam curtain between said concave and convex reflectors;

said concave and convex reflectors and said laser source being arranged such that a pitch of the laser beam segments multi-reflected in said reflection space to form the laser curtain between said concave and convex reflectors becomes much closer in such a manner that the multi-reflected beam segments are overlapped with respect to each other, to enhance a light intensity thereof;

adjustment means for adjusting a relative position between said concave and convex reflectors in two directions perpendicular to each other and to a common optical axis of said concave and convex reflectors, said adjustment means including a deformable support structure for said convex and concave reflectors, and means for exerting a deforming force on said deformable support structure such that one of said convex and concave reflectors is moved relative to and in parallel to the other reflector along at least one of said two directions, whereby the arrangement of said concave and convex reflectors and said laser source for obtaining the required laser beam curtain can be easily made without an angular adjustment of said concave and convex reflectors; and detection means for detecting light scattered due to a presence of particles in the laser beam curtain between said concave and convex reflectors, whereby the presence of particles can be detected with a high probability and a high sensitivity.

2. An optoelectrical particle detection apparatus according to claim 1, wherein the laser beam is emitted from said reflection space at a side opposite to the side from which the laser beam is introduced into said reflection space.

3. An optoelectrical particle detection apparatus according to claim 1, wherein the laser beam is emitted from said reflection space at the same side from which the laser beam is introduced into said reflection space.

4. A optoelectrical particle detection apparatus according to claim 1, wherein said laser source comprises a semiconductor laser device so that an interference of the overlapped multi-reflected beam segments is eliminated, and wherein a relatively narrow band of said laser beam curtain, a light intensity of which is relatively uniform, is selected as a detection zone, whereby not only the presence of particles is able to be detected, but also a size of the detected particle is able to be measured.

5. A optoelectrical particle detection apparatus according to claim 1, wherein said detection means includes an optical filter by which a noise is eliminated from the light detected by said detection means.

6. A optoelectrical particle detection apparatus according to claim 1, wherein said apparatus is used to detect a floating particle in a vacuum chamber for a thin-film forming process, an assembly of said concave and convex reflectors and said laser source being disposed within said vacuum chamber and being housed in a housing in such a manner that said laser beam curtain is exposed to the exterior of said housing, an inert gas being introduced into said housing, whereby pollution of said concave and convex reflectors by particles generated during said thin-film forming process is prevented.

7. A optoelectrical particle detection apparatus according to claim 6, wherein said detection means includes an optical filter by which light generated during said thin-film forming process is eliminated from the light detected by said detection means.

8. A optoelectrical particle detection apparatus according to claim 7, wherein said bundle of optical fibers is covered by a tube sealingly passed through the wall of said vacuum chamber.

9. A optoelectrical particle detection apparatus according to claim 6, wherein said detection means includes a light detector disposed outside said vacuum chamber, and a bundle of optical fibers accessed to said laser beam curtain through a wall defining said vacuum chamber to transmit the scattered light received thereby to said light detector.

10. An optoelectrical particle detection apparatus according to claim 1, wherein said apparatus is used to detect a floating particle in a vacuum chamber for a thin-film forming process, an assembly of said concave and convex reflectors and said laser source being disposed within said vacuum chamber, wherein said detection means is associated with a control means for controlling said thin-film forming process so that a generation of particles is avoided.

11. An optoelectrical particle detection apparatus according to claim 10, wherein said thin-film forming process is a sputtering process, said assembly being housed in a housing in such a manner that said laser beam curtain is exposed to the exterior of said housing, an inert gas being introduced into said housing, whereby pollution of said concave and convex reflectors by particles generated during said sputtering process is prevented.

12. An optoelectrical particle detection apparatus comprising:

concave and convex reflectors having concave and convex reflecting surfaces, respectively, and spaced from each other by a predetermined distance to form a reflection space therebetween, the reflecting surface of said concave reflector having a spherical concave reflecting surface zone and a plane reflecting surface zone smoothly continuing therefrom the reflecting surface of said convex reflector having a spherical convex reflecting surface zone and a plane reflecting surface zone smoothly continuing therefrom;

a laser source for emitting a laser beam and introducing the laser beam into said reflection space through the spherical concave and convex reflecting surface zones of said concave and convex reflectors to be multi-reflected to form a laser beam curtain therebetween;

said concave and convex reflectors and said laser source being arranged so that a pitch of the laser beam segments multi-reflected to form the laser beam curtain between the spherical concave and convex reflecting surface zones of said concave and convex reflectors becomes much closer, and so that the much closer pitch of the laser beam segments multi-reflected to form the laser beam curtain between the plane reflecting surface zones of said concave and convex reflectors is uniformly maintained, whereby the laser beam curtain formed by the laser beam segments multi-reflected between the plane reflecting surface zones of said concave and convex reflectors has a substantially uniform distribution of light intensity;

adjustment means for adjusting a relative position between said concave and convex reflectors in two directions perpendicular to each other and to a common optical axis of said concave and convex reflectors, said adjustment means including a deformable support structure for said convex and concave reflectors, and means for exerting a deforming force on said deformable support structure such that one of said convex and concave reflectors is moved relative to and in parallel to the other reflector along at least one of said two directions, whereby the arrangement of said concave and convex reflectors and said laser source for obtaining the required laser beam curtain can be easily made without an angular adjustment of said concave and convex reflectors; and detection means for detecting light scattered due to a presence of particles in the portion of said laser beam curtain between the plane reflecting surface zones of said concave and convex reflectors, whereby not only can the presence of particles be detected, but also a size of the detected particles can be 13. A optoelectrical particle detection apparatus according to claim 12, wherein said detection means includes an optical filter by which a noise is eliminated from the light detected by said detection means.

14. A optoelectrical particle detection apparatus according to claim 12, wherein said apparatus is used to detect a floating particle in a vacuum chamber for a thin-film forming process, an assembly of said concave and convex reflectors and said laser source being disposed within said vacuum chamber and being housed in a housing in such a manner that said laser beam curtain is exposed to the exterior of said housing, an inert gas being introduced into said housing, whereby pollution of said concave and convex reflectors by particles generated during said thin-film forming process is prevented.

15. A optoelectrical particle detection apparatus according to claim 14, wherein said detection means includes an optical filter by which light generated during said thin-film forming process is eliminated from the light detected by said detection means.

16. A optoelectrical particle detection apparatus according to claim 14, wherein said detection means includes a light detector disposed outside said vacuum chamber, and a bundle of optical fibers accessed to said laser beam curtain through a wall defining said vacuum chamber to transmit the scattered light received thereby to said light detector.

17. A optoelectrical particle detection apparatus according to claim 12, wherein said bundle of optical fibers is covered by a tube sealingly passed through the wall of said vacuum chamber.

* * * * *

UNITED STATES PATENT AND TRADEMARK OFFICE
CERTIFICATE OF CORRECTION

PATENT NO. : 5,094,533

DATED : March 10, 1992

INVENTOR(S) : SHIGETOMO SAWADA, and KAZUO KOBAYASHI

It is certified that error appears in the above-identified patent and that said Letters Patent is hereby corrected as shown below:

```
Column 1,    line 16, "semi-conductors" should be
                      --semiconductors--.
Column 5,    line 32, "an" should be --a--.
Column 9,    line 4,  "e,crc/1/1" should be --①--.
Column 11,   line 32, e,crc/1/1" should be --①--.
Column 12,   line 45, "bean" should be --beam--.
Column 15,   line 6,  "prove" should be --probe--.
Column 16,   line 54, "Ne-Ne" should be --He-Ne--.
Column 17,   line 13, "sued" should be --used--;
             line 34, after "shown" insert --in--.
Column 19,   line 12, after "it" insert --is--.
Column 20,   line 23, delete "is";
             line 58, delete "is".
Column 25,   line 67, "A" should be --An--.
Column 26,   line 9,  "A" should be --An--;
             line 13, "A" should be --An--;
             line 25, "A" should be --An--;
             line 30, "A" should be --An--;
             line 34, "A" should be --An--.
```

UNITED STATES PATENT AND TRADEMARK OFFICE
CERTIFICATE OF CORRECTION

PATENT NO. : 5,094,533
DATED : March 10, 1992
INVENTOR(S) : Shigetomo Sawada, and Kazuo Kobayashi It is certified that error appears in the above-indentified patent and that said Letters Patent is hereby corrected as shown below:

Column 28, line 7, after "be" insert --measured.--;
            line 8, "A" should be --An--;
            line 12, "A" should be --An--;
            line 24, "A" should be --An--;
            line 29, "A" should be --An--;
            line 36, "A" should be --An--.

Signed and Sealed this

Twenty-sixth Day of October, 1993

*Attest:*

BRUCE LEHMAN

*Attesting Officer*     *Commissioner of Patents and Trademarks*